United States Patent
Fleischer et al.

(10) Patent No.: US 11,339,428 B2
(45) Date of Patent: May 24, 2022

(54) INCREASED SIGNAL TO NOISE IN NUCLEIC ACID SEQUENCING

(71) Applicant: Omniome, Inc., San Diego, CA (US)

(72) Inventors: Chad Fleischer, San Diego, CA (US); Denis Malyshev, La Jolla, CA (US)

(73) Assignee: PACIFIC BIOSCIENCES OF CALIFORNIA, INC., Menlo Park, CA (US)

( * ) Notice: Subject to any disclaimer, the term of this patent is extended or adjusted under 35 U.S.C. 154(b) by 365 days.

(21) Appl. No.: 16/383,279

(22) Filed: Apr. 12, 2019

(65) Prior Publication Data

US 2019/0367974 A1 Dec. 5, 2019

Related U.S. Application Data

(60) Provisional application No. 62/678,434, filed on May 31, 2018.

(51) Int. Cl.

| | | |
|---|---|---|
| C12Q 1/6869 | (2018.01) | |
| C12N 9/12 | (2006.01) | |
| C12Q 1/6806 | (2018.01) | |
| C12Q 1/6809 | (2018.01) | |
| C12Q 1/6811 | (2018.01) | |
| C12Q 1/6853 | (2018.01) | |
| C12Q 1/686 | (2018.01) | |

(52) U.S. Cl.
CPC ......... *C12Q 1/6869* (2013.01); *C12N 9/1252* (2013.01); *C12Q 1/6806* (2013.01); *C12Q 1/686* (2013.01); *C12Q 1/6809* (2013.01); *C12Q 1/6811* (2013.01); *C12Q 1/6853* (2013.01); *C12Q 2521/101* (2013.01); *C12Q 2521/501* (2013.01); *C12Q 2525/186* (2013.01); *C12Q 2527/125* (2013.01); *C12Q 2535/113* (2013.01); *C12Q 2537/137* (2013.01); *C12Q 2537/161* (2013.01); *C12Q 2537/163* (2013.01)

(58) Field of Classification Search
CPC .... C12Q 1/6869; C12Q 1/6853; C12Q 1/686; C12Q 2535/113; C12Q 2525/186; C12Q 2527/125; C12Q 2521/101
See application file for complete search history.

(56) References Cited

U.S. PATENT DOCUMENTS

| | | |
|---|---|---|
| 7,057,026 B2 | 6/2006 | Barnes et al. |
| 7,211,414 B2 | 5/2007 | Hardin et al. |
| 7,264,934 B2 | 9/2007 | Fuller |
| 7,315,019 B2 | 1/2008 | Turner et al. |
| 7,405,281 B2 | 7/2008 | Xu et al. |
| 7,414,116 B2 | 8/2008 | Milton et al. |
| 7,427,673 B2 | 9/2008 | Balasubramanian et al. |
| 7,482,120 B2 | 1/2009 | Buzby |
| 7,544,794 B1 | 6/2009 | Benner et al. |
| 7,906,284 B2 | 3/2011 | Turner et al. |
| 7,956,171 B2 | 6/2011 | Siddiqi et al. |
| 8,034,923 B1 | 10/2011 | Benner et al. |
| 8,071,755 B2 | 12/2011 | Efcavitch et al. |
| 8,399,196 B2 | 3/2013 | Hoser |
| 8,632,975 B2 | 1/2014 | Vander Horn et al. |
| 8,652,781 B2 | 2/2014 | Korlach et al. |
| 9,279,154 B2 | 6/2016 | Previte et al. |
| 9,399,798 B2 | 7/2016 | Morris et al. |
| 9,453,258 B2 | 9/2016 | Kain et al. |
| 9,951,385 B1 | 4/2018 | Vijayan et al. |
| 10,077,470 B2 | 9/2018 | Vijayan et al. |
| 10,161,003 B2 | 12/2018 | Stromberg et al. |
| 10,246,744 B2 | 4/2019 | Vijayan et al. |
| 10,253,352 B2 | 4/2019 | Nguyen et al. |
| 10,400,272 B1 | 9/2019 | Middleton et al. |
| 2002/0072053 A1 | 6/2002 | McNally et al. |
| 2005/0130173 A1 | 6/2005 | Leamon et al. |
| 2006/0134633 A1 | 6/2006 | Chen et al. |
| 2008/0108082 A1 | 5/2008 | Rank et al. |
| 2009/0029421 A1 | 1/2009 | Piepenburg et al. |
| 2009/0191553 A1 | 7/2009 | Hendrickson |

(Continued)

FOREIGN PATENT DOCUMENTS

| | | |
|---|---|---|
| WO | 9106678 | 5/1991 |
| WO | 2004018497 | 3/2004 |

(Continued)

OTHER PUBLICATIONS

Bentley et al., "Accurate Whole Human Genome Sequencing Using Reversible Terminator Chemistry", Nature, vol. 456, No. 7218, Nov. 6, 2008, pp. 53-59.
Turcatti et al., "A new class of cleavable fluorescent nucleotides: synthesis and optimization as reversible terminators for DNA sequencing by synthesis", Nucleic acids research 36.4, e25, 2008, 13 pages.
U.S. Appl. No. 16/657,051, "Final Office Action", dated Feb. 18, 2021, 22 pages.
U.S. Appl. No. 16/657,051, Advisory Action, dated Aug. 4, 2020, 5 pages.
Cetin et al., "Plasmonic Sensor Could Enable Label-Free DNA Sequencing", ACS Sensors, vol. 3, No. 3, 2018, pp. 561-568.
PCT/US2019/056957, International Search Report and Written Opinion, dated Jul. 13, 2020, 13 pages.

(Continued)

*Primary Examiner* — Angela M. Bertagna
(74) *Attorney, Agent, or Firm* — Kilpatrick Townsend & Stockton LLP

(57) ABSTRACT

A method for identifying a nucleotide in a template nucleic acid by (a) providing a plurality of primer-template nucleic acid hybrids, wherein the primers have an extendable 3' end; (b) contacting the plurality with: (i) blocked nucleotides to produce a first subset of the primer-template nucleic acid hybrids that include a blocked nucleotide at the 3' end, and (ii) a ternary complex inhibitor to produce a second subset of the primer-template nucleic acid hybrids that include a ternary complex inhibitor; (c) forming ternary complexes that each include a polymerase, a primer-template nucleic acid hybrid of the first subset, and a cognate nucleotide; and (d) detecting the ternary complexes, thereby identifying a nucleotide in the template nucleic acid.

18 Claims, No Drawings

(56) References Cited

U.S. PATENT DOCUMENTS

| | | |
|---|---|---|
| 2010/0111768 A1 | 5/2010 | Banerjee et al. |
| 2012/0070838 A1* | 3/2012 | Xi .................... C12Q 1/6853 |
| | | 435/6.12 |
| 2012/0270305 A1 | 10/2012 | Reed et al. |
| 2017/0022553 A1 | 1/2017 | Vijayan et al. |
| 2017/0314064 A1 | 11/2017 | Tyidogan et al. |
| 2018/0044715 A1 | 2/2018 | Tyidogan et al. |
| 2018/0044727 A1 | 2/2018 | Vijayan et al. |
| 2018/0187245 A1 | 7/2018 | Dambacher et al. |
| 2018/0208983 A1 | 7/2018 | Dambacher et al. |
| 2019/0048404 A1 | 2/2019 | Dambacher |

FOREIGN PATENT DOCUMENTS

| | | |
|---|---|---|
| WO | 2005065814 | 7/2005 |
| WO | 2007123744 | 11/2007 |
| WO | 2018035134 | 2/2018 |

OTHER PUBLICATIONS

PCT/US2019/027292, "International Search Report and Written Opinion", dated Jun. 4, 2019, 13 pages.
U.S. Appl. No. 16/657,051, "Non-Final Office Action", dated Apr. 8, 2020, 15 pages.
U.S. Appl. No. 16/657,051, "Final Office Action", dated May 20, 2020, 23 pages.
Metzker, "Sequencing Technologies—The Next Generation", Nature Reviews Genetics, vol. 11, No. 1, Jan. 2010, pp. 31-46.

* cited by examiner

INCREASED SIGNAL TO NOISE IN NUCLEIC ACID SEQUENCING

CROSS-REFERENCE TO RELATED APPLICATION

This application is based on, and claims the benefit of, U.S. Provisional Application No. 62/678,434, filed May 31, 2018, which is incorporated herein by reference in its entirety.

BACKGROUND

The present disclosure relates generally to characterization of nucleic acids and has specific applicability to nucleic acid sequencing.

Several commercial, nucleic acid sequencing techniques are performed using nucleic acid ensembles. The ensembles are generally produced by amplification techniques that yield a localized collection of nucleic acid copies that are manipulated and detected as a whole. Exemplary techniques for creating ensembles include bridge amplification techniques used by Illumina platforms (San Diego, Calif.), emulsion polymerase chain reaction techniques used by Ion Torrent platforms (Thermo Fisher, Waltham Mass.), and rolling circle techniques used by Complete Genomics platforms (BGI, Shenzhen China). Ensembles provide a benefit of higher signal amplitude compared to single molecule sequencing techniques and minimization of artifacts that arise from stochastic noise when manipulating and detecting single molecules.

Despite broad adoption of ensemble-based sequencing techniques, so called "phasing" limits read length, overall throughput and accuracy. Phasing is the phenomenon whereby individual molecules within the ensemble lose sync with each other. Phasing can manifest as extension of one or more primer molecules falling behind the others in the ensemble or as extension of one or more primer molecules going ahead of others in the ensemble. Phasing is pernicious and cumulative. A phasing rate of only 0.5% per cycle results in an accumulated loss of roughly half of true signal after 120 cycles. The problem is exacerbated by the proportional increase in background noise due to the false signals that arise from members of the ensemble that are out of phase. The accumulated loss in signal-to-noise results in a limitation on read length (which, in turn, results in reduced sequencing throughput) and increased errors especially for later cycles as noise overwhelms signal.

Thus, there exists a need for methods that reduce or prevent phasing in ensemble-based sequencing. The present invention satisfies this need and provides other advantages as well.

BRIEF SUMMARY

The present disclosure provides a method for identifying a nucleotide in a template nucleic acid. The method can include steps of (a) providing a plurality of primer-template nucleic acid hybrids, wherein the primers have an extendable 3' end; (b) contacting the plurality with: (i) blocked nucleotides to produce a first subset of the primer-template nucleic acid hybrids that include a blocked nucleotide at the 3' end, and (ii) a ternary complex inhibitor to produce a second subset of the primer-template nucleic acid hybrids that include a ternary complex inhibitor; (c) forming ternary complexes that each include a polymerase, a primer-template nucleic acid hybrid of the first subset, and a cognate nucleotide; and (d) detecting the ternary complexes, thereby identifying a nucleotide in the template nucleic acid. Optionally the blocked nucleotides can be reversibly terminated nucleotides.

Also provided is a method for identifying a nucleotide in a template nucleic acid that includes steps of (a) providing a plurality of primer-template nucleic acid hybrids, wherein the primers have an extendable 3' end; (b) incorporating a blocked nucleotide at the 3' end of the primer(s) of a first subset of the primer-template nucleic acid hybrids; (c) incorporating a ternary complex inhibitor at the 3' end of the primer(s) of a second subset of the primer-template nucleic acid hybrids; (d) forming ternary complexes that each include a polymerase, a primer-template nucleic acid hybrid of the first subset, and a cognate nucleotide; and (e) detecting the ternary complexes, thereby identifying a nucleotide in the template nucleic acid. Optionally the blocked nucleotides can be reversibly terminated nucleotides.

The present disclosure provides a method for sequencing a template nucleic acid. The method can include steps of (a) providing a plurality of primer-template nucleic acid hybrids, wherein the primers have an extendable 3' end; (b) contacting the plurality with: (i) reversibly terminated nucleotides to produce a first subset of the primer-template nucleic acid hybrids that include a reversibly terminated nucleotide at the 3' end, and (ii) a ternary complex inhibitor to produce a second subset of the primer-template nucleic acid hybrids that include a ternary complex inhibitor; (c) forming ternary complexes that each include a polymerase, a primer-template nucleic acid hybrid of the first subset, and a cognate nucleotide; (d) detecting the ternary complexes, thereby identifying a nucleotide in the template nucleic acid; (e) deblocking the reversibly terminated nucleotide at the 3' end of the primer-template nucleic acid hybrids in the first subset; and (f) repeating steps (b) through (e) to sequence template nucleic acids in the first subset.

A method for sequencing a template nucleic acid can include steps of (a) providing a plurality of primer-template nucleic acid hybrids, wherein the primers have an extendable 3' end; (b) incorporating a blocked nucleotide at the 3' end of the primer(s) of a first subset of the primer-template nucleic acid hybrids; (c) incorporating a ternary complex inhibitor at the 3' end of the primer(s) of a second subset of the primer-template nucleic acid hybrids; (d) forming ternary complexes that each include a polymerase, a primer-template nucleic acid hybrid of the first subset, and a cognate nucleotide; (e) detecting the ternary complexes, thereby identifying a nucleotide in the template nucleic acid; (f) deblocking the reversibly terminated nucleotide at the 3' end of the primer-template nucleic acid hybrids in the first subset; and (g) repeating steps (b) through (f) to sequence template nucleic acids in the first subset.

The present disclosure further provides an apparatus that includes a plurality of primer-template nucleic acid hybrids, wherein a first subset of the primer-template nucleic acid hybrids has a blocked nucleotide at the 3' end of the primer, and wherein a second subset of the primer-template nucleic acid hybrids has a ternary complex inhibitor at the 3' end of the primer. Optionally, the blocked nucleotide can be a reversibly terminated nucleotide.

DETAILED DESCRIPTION

The present disclosure provides methods for identifying a nucleotide base that is present at an interrogation position in a primer-template nucleic acid hybrid. The interrogated position is the base located immediately 5' of the base in the template that is hybridized to the 3' end of the primer. The nucleotide that is present at the interrogation position can be identified in an examination step that is used to detect a ternary complex that forms between the primer-template nucleic acid hybrid, polymerase and a nucleotide cognate for the base at the interrogation position. The polymerase functions to pair the cognate nucleotide with the next base of the template. The identity of the base at the interrogation position can be determined by distinguishing the type of nucleotide that is present in the ternary complex and inferring the template base to which it hybridizes in accordance with Watson Crick base pairing.

In particular embodiments, the primer can be incrementally extended in order to shift the interrogation position along the template. For example, the sequence of the template can be determined by a series of cycles in which the primer is extended by a single nucleotide to shift to the next template position for interrogation, and examination is carried out at the new interrogation position. Incomplete extension can lead to sequencing errors or premature termination of the sequencing process. Phasing problems also manifest, for example, when a population of primer-template nucleic acid hybrids is sequenced as an ensemble.

The present disclosure provides methods and compositions that can be useful for improving identification of bases in nucleic acids, for example, in a sequencing method. Improvement can be achieved by including a primer modification process that caps primers that are not to be subsequently detected. For example, primers that are not extended in a primer extension step can be capped so that the non-extended primers do not contribute to errors in subsequent examination steps. For embodiments in which template nucleotides are identified by examination of ternary complexes, a particularly useful cap is provided by a ternary complex inhibitor. The ternary complex inhibitor can be a moiety that, when attached to the primer, prevents a polymerase and/or cognate nucleotide from participating in formation or maintenance of a ternary complex at the end of the modified primer. A ternary complex inhibitor can be present at the end of a primer, for example, as a moiety that creates a steric block to one or more components that would otherwise form a ternary complex, or as a moiety that creates a charge that repels one or more of the components.

By way of example, inhibition of ternary complex formation can result when the primer is fully extended such that no template positions are accessible for forming a ternary complex. Full extension can be manifest as the 3' end of the extended primer being annealed to the 5' end of the template. In this configuration the double stranded extension product does not contain a next template base that is unpaired. In an alternative configuration, full extension can manifest as a primer that is extended until further extension is prevented by factors in the environment of the extension product. In this configuration, the template may contain an unpaired next template base, but the next template base is inaccessible to polymerase (and/or inaccessible to next correct nucleotide) due to the environment around the template and extended primer. For example, the 5' end of the template can be attached to a solid-phase surface such and the 3' end of the extended primer is so close to the surface that polymerase is not only prevented from further extension but is also prevented from binding to form a ternary complex. In both of these examples, full extension has produced an oligonucleotide moiety that functions as a cap on the extended primer.

In some configurations, a ternary complex inhibitor moiety can be a first binding partner (e.g. a ligand) that has binding affinity for a second binding partner (e.g. a receptor such as an antibody). Whether or not the first binding partner is capable of inhibiting formation of a ternary complex, inhibition can result when the second binding partner is bound to the first binding partner. The ternary complex inhibitor can be present at the 3' end of a primer, for example, as a result of extending the 3' end of the primer with a nucleotide analog, the nucleotide analog being attached to the first binding partner. In this configuration, the complex between the first and second binding partners functions as a cap on the extended primer.

In an alternative embodiment, a primer modification process can be used to remove a primer such that it will not participate in a subsequent detection step. For example, a primer that is not extended in a primer extension step can be degraded chemically or enzymatically (e.g. via an exonuclease) so that the non-extended primer does not form a ternary complex that would contribute to errors in subsequent examination steps.

Terms used herein will be understood to take on their ordinary meaning in the relevant art unless specified otherwise. Several terms used herein, and their meanings, are set forth below.

As used herein, the term "array" refers to a population of molecules that are attached to one or more solid support such that the molecules at one feature can be distinguished from molecules at other features. An array can include different molecules that are each located at different addressable features on a solid support. Alternatively, an array can include separate solid supports each functioning as a feature that bears a different molecule, wherein the different molecules can be identified according to the locations of the solid supports on a surface to which the solid supports are attached, or according to the locations of the solid supports in a liquid such as a fluid stream. The molecules of the array can be, for example, nucleotides, nucleic acid primers, nucleic acid templates or nucleic acid enzymes such as polymerases, ligases, exonucleases or combinations thereof.

As used herein, the term "blocking moiety," when used in reference to a nucleotide, means a part of the nucleotide that inhibits or prevents the 3' oxygen of the nucleotide from forming a covalent linkage to a next correct nucleotide during a nucleic acid polymerization reaction. The blocking moiety of a "reversibly terminated" nucleotide can be removed from the nucleotide analog, or otherwise modified, to allow the 3'-oxygen of the nucleotide to covalently link to a next correct nucleotide. Such a blocking moiety is referred to herein as a "reversible terminator moiety." Exemplary reversible terminator moieties are set forth in U.S. Pat. Nos. 7,427,673; 7,414,116; 7,057,026; 7,544,794 or 8,034,923; or PCT publications WO 91/06678 or WO 07/123744, each of which is incorporated herein by reference. A nucleotide that has a blocking moiety or reversible terminator moiety can be at the 3' end of a nucleic acid, such as a primer, or can be a monomer that is not covalently attached to a nucleic acid. A blocking moiety need not hinder or preclude ternary complex formation at the 3' end of a nucleic acid to which the blocking moiety is attached. A particularly useful blocking moiety will be present at the 3' end of a nucleic acid that participates in formation of a ternary complex.

As used herein, the term "catalytic metal ion" refers to a metal ion that facilitates phosphodiester bond formation between the 3'-oxygen of a nucleic acid (e.g., a primer) and the phosphate of an incoming nucleotide by a polymerase. A "divalent catalytic metal cation" is a catalytic metal ion having a valence of two. Catalytic metal ions can be present at concentrations that stabilize formation of a complex between a polymerase, nucleotide, and primed template nucleic acid, referred to as non-catalytic concentrations of a metal ion insofar as phosphodiester bond formation does not occur. Catalytic concentrations of a metal ion refer to the amount of a metal ion sufficient for polymerases to catalyze the reaction between the 3'-oxygen of a nucleic acid (e.g., a primer) and the phosphate group of an incoming nucleotide.

As used herein, the term "common sequence" means a sequence of nucleotides that is the same for two or more nucleic acid molecules. The sequence that is common to two or more nucleic acids can include all or part of the nucleic acids that are being compared. The common sequence can have a length of at least 5, 10, 25, 50, 100, 250, 500, 1000 or more nucleotides. Alternatively or additionally, the length can be at most 1000, 500, 250, 100, 50, 25, 10, or 5 nucleotides.

The term "comprising" is intended herein to be open-ended, including not only the recited elements, but further encompassing any additional elements.

As used herein, the term "deblock" means to remove or modify a reversible terminator moiety of a nucleotide to render the nucleotide extendable. For example, the nucleotide can be present at the 3' end of a primer such that deblocking renders the primer extendable. Exemplary deblocking reagents and methods are set forth in U.S. Pat. Nos. 7,427,673; 7,414,116; 7,057,026; 7,544,794 or 8,034,923; or PCT publications WO 91/06678 or WO 07/123744, each of which is incorporated herein by reference.

As used herein, the term "detect as an ensemble" means to detect a characteristic of a population of molecules under conditions that do not necessarily distinguish one molecule of the population from other molecules in the population. For example, a population of nucleic acids that is detected as an ensemble at a feature of an array can produce an apparent characteristic that is a composite of characteristics for the nucleic acids at the feature. The characteristic can be a luminescent signal that is an average of luminescence from multiple luminophores at a feature of an array.

As used herein, the term "each," when used in reference to a collection of items, is intended to identify an individual item in the collection but does not necessarily refer to every item in the collection. Exceptions can occur if explicit disclosure or context clearly dictates otherwise.

As used herein, the term "exogenous," when used in reference to a moiety of a molecule, means a chemical moiety that is not present in a natural analog of the molecule. For example, an exogenous label of a nucleotide is a label that is not present on a naturally occurring nucleotide. Similarly, an exogenous label that is present on a polymerase is not found on the polymerase in its native milieu.

As used herein, the term "extension," when used in reference to a nucleic acid, means a process of adding at least one nucleotide to the 3' end of the nucleic acid. The term "polymerase extension," when used in reference to a nucleic acid, refers to a polymerase catalyzed process of adding at least one nucleotide to the 3' end of the nucleic acid. A nucleotide or oligonucleotide that is added to a nucleic acid by extension is said to be incorporated into the nucleic acid. Accordingly, the term "incorporating" can be used to refer to the process of joining a nucleotide or oligonucleotide to the 3' end of a nucleic acid by formation of a phosphodiester bond.

As used herein, the term "extendable," when used in reference to a nucleotide, means that the nucleotide has an oxygen or hydroxyl moiety at the 3' position, and is capable of forming a covalent linkage to a next correct nucleotide if and when incorporated into a nucleic acid. An extendable nucleotide can be at the 3' position of a primer or it can be a monomeric nucleotide. A nucleotide that is extendable will lack blocking moieties such as reversible terminator moieties.

As used herein, the term "feature," when used in reference to an array, means a location in an array where a particular molecule is present. A feature can contain only a single molecule or it can contain a population of several molecules of the same species (i.e. an ensemble of the molecules). Alternatively, a feature can include a population of molecules that are different species (e.g. a population of ternary complexes having different template sequences). Features of an array are typically discrete. The discrete features can be contiguous or they can have spaces between each other. An array useful herein can have, for example, features that are separated by less than 100 microns, 50 microns, 10 microns, 5 microns, 1 micron, or 0.5 micron. Alternatively or additionally, an array can have features that are separated by greater than 0.5 micron, 1 micron, 5 microns, 10 microns, 50 microns or 100 microns. The features can each have an area of less than 1 square millimeter, 500 square microns, 100 square microns, 25 square microns, 1 square micron or less.

As used herein, the term "label" refers to a molecule, or moiety thereof, that provides a detectable characteristic. The detectable characteristic can be, for example, an optical signal such as absorbance of radiation, fluorescence emission, luminescence emission, fluorescence lifetime, fluorescence polarization, or the like; Rayleigh and/or Mie scattering; binding affinity for a ligand or receptor; magnetic properties; electrical properties; charge; mass; radioactivity or the like. Exemplary labels include, without limitation, a fluorophore, luminophore, chromophore, nanoparticle (e.g., gold, silver, carbon nanotubes), heavy atoms, radioactive isotope, mass label, charge label, spin label, receptor, ligand, or the like.

As used herein, a "manufactured vessel" is a container that is human-made or human-modified and that functions to isolate one chemical process (e.g., a binding event; an incorporation reaction; etc.) from another, or to provide a space in which a chemical process can take place. Non-limiting examples of manufactured vessels useful in connection with the disclosed technique include: flow cells, wells of a multi-well plate; microscope slides; tubes (e.g., capillary tubes); etc. Features to be examined or detected can be contained within the reaction vessel.

As used herein, the term "next correct nucleotide" refers to the nucleotide type that will bind and/or incorporate at the 3' end of a primer to complement a base in a template strand to which the primer is hybridized. The base in the template strand is referred to as the "next base" and is immediately 5' of the base in the template that is hybridized to the 3' end of the primer. The next correct nucleotide can be referred to as the "cognate" of the next base and vice versa. Cognate nucleotides that interact with each other in a ternary complex or in a double stranded nucleic acid are said to "pair" with each other. A nucleotide having a base that is not complementary to the next template base is referred to as an "incorrect", "mismatch" or "non-cognate" nucleotide.

As used herein, the term "non-catalytic metal ion" refers to a metal ion that, when in the presence of a polymerase enzyme, does not facilitate phosphodiester bond formation needed for chemical incorporation of a nucleotide into a primer. A non-catalytic metal ion may interact with a polymerase, for example, via competitive binding compared to catalytic metal ions. Accordingly, a non-catalytic metal ion can act as an inhibitory metal ion. A "divalent non-catalytic metal ion" is a non-catalytic metal ion having a valence of two. Examples of divalent non-catalytic metal ions include, but are not limited to, $Ca^{2+}$, $Zn^{2+}$, $Co^{2+}$, $Ni^{2+}$, and $Sr^{2+}$. The trivalent $Eu^{3+}$ and $Tb^{3+}$ ions are non-catalytic metal ions having a valence of three.

As used herein, the term "nucleotide" can be used to refer to a native nucleotide or analog thereof. Examples include, but are not limited to, nucleotide triphosphates (NTPs) such as ribonucleotide triphosphates (rNTPs), deoxyribonucleotide triphosphates (dNTPs), or non-natural analogs thereof such as dideoxyribonucleotide triphosphates (ddNTPs) or reversibly terminated nucleotide triphosphates (rtNTPs).

As used herein, the term "oligonucleotide moiety" refers to a portion of a nucleic acid that includes at least 2 contiguous nucleotides. An oligonucleotide moiety can include, for example, at least 5, 8, 10, 15, 20, 25, 50, 100 or more contiguous nucleotides. Alternatively or additionally, an oligonucleotide moiety can include at most 100, 50, 25, 20, 15, 10, 8, 5 or 2 contiguous nucleotides. In some embodiments, an oligonucleotide moiety that is added to a primer-template hybrid can have a length that is equivalent to the length of the template from the next template nucleotide to the 5' end of the template.

As used herein, the term "polymerase" can be used to refer to a nucleic acid synthesizing enzyme, including but not limited to, DNA polymerase, RNA polymerase, reverse transcriptase, primase and transferase. Typically, the polymerase has one or more active sites at which nucleotide binding and/or catalysis of nucleotide polymerization may occur. The polymerase may catalyze the polymerization of nucleotides to the 3' end of the first strand of the double stranded nucleic acid molecule. For example, a polymerase catalyzes the addition of a next correct nucleotide to the 3' oxygen group of the first strand of the double stranded nucleic acid molecule via a phosphodiester bond, thereby covalently incorporating the nucleotide to the first strand of the double stranded nucleic acid molecule. Optionally, a polymerase need not be capable of nucleotide incorporation under one or more conditions used in a method set forth herein. For example, a mutant polymerase may be capable of forming a ternary complex but incapable of catalyzing nucleotide incorporation.

As used herein, the term "primer-template nucleic acid hybrid" or "primer-template hybrid" refers to a nucleic acid having a double stranded region such that one of the strands is a primer and the other strand is a template. The two strands can be parts of a contiguous nucleic acid molecule (e.g. a hairpin structure) or the two strands can be separable molecules that are not covalently attached to each other.

As used herein, the term "primer" refers to a nucleic acid having a sequence that binds to a nucleic acid at or near a template sequence. Generally, the primer binds in a configuration that allows replication of the template, for example, via polymerase extension of the primer. The primer can be a first portion of a nucleic acid molecule that binds to a second portion of the nucleic acid molecule, the first portion being a primer sequence and the second portion being a primer binding sequence (e.g. a hairpin primer). Alternatively, the primer can be a first nucleic acid molecule that binds to a second nucleic acid molecule having the template sequence. A primer can consist of DNA, RNA or analogs thereof. A primer can have an extendible 3' end, a 3' end that is blocked from primer extension or a 3' end that is capped to hinder or preclude ternary complex formation.

As used herein, the term "solid support" refers to a rigid substrate that is insoluble in aqueous liquid. The substrate can be non-porous or porous. The substrate can optionally be capable of taking up a liquid (e.g. due to porosity) but will typically be sufficiently rigid that the substrate does not swell substantially when taking up the liquid and does not contract substantially when the liquid is removed by drying. A nonporous solid support is generally impermeable to liquids or gases. Exemplary solid supports include, but are not limited to, glass and modified or functionalized glass, plastics (including acrylics, polystyrene and copolymers of styrene and other materials, polypropylene, polyethylene, polybutylene, polyurethanes, Teflon™, cyclic olefins, polyimides etc.), nylon, ceramics, resins, Zeonor, silica or silica-based materials including silicon and modified silicon, carbon, metals, inorganic glasses, optical fiber bundles, and polymers.

As used herein, the term "subset" means a collection of one or more things, all of which are contained in a larger collection of things. The larger collection of things can be referred to as a "set". A subset can include at least 1, 2, 10, 100, $1\times10^3$, $1\times10^6$, $1\times10^9$ or more things. The things can be, for example, nucleic acids such as primer-template nucleic acid hybrids, ternary complexes, polymerases, nucleotides or other compositions set forth herein.

As used herein, the term "ternary complex" refers to an intermolecular association between a polymerase, a double stranded nucleic acid and a nucleotide. Typically, the polymerase facilitates interaction between a next correct nucleotide and a template strand of the primed nucleic acid. A next correct nucleotide can interact with the template strand via Watson-Crick hydrogen bonding. The term "stabilized ternary complex" means a ternary complex having promoted or prolonged existence or a ternary complex for which disruption has been inhibited. Generally, stabilization of the ternary complex prevents covalent incorporation of the nucleotide component of the ternary complex into the primed nucleic acid component of the ternary complex.

As used herein, the term "ternary complex inhibitor" refers to a moiety that when present in a nucleic acid hinders or precludes the nucleic acid from binding to a polymerase and/or nucleotide to form a ternary complex. Moieties that create a steric block to ternary complex formation are particularly useful and include, for example, a polymerization or ligation product that extends a primer to the end of a template to which the primer is hybridized. Another example of a steric block is a mismatched nucleotide. Moieties can also be used to introduce a positive or negative charge that hinders or prevents ternary complex formation. A moiety can be a ligand that will bind to a receptor that hinders or prevents ternary complex formation such as a biotin (or analog thereof) that binds to streptavidin (or an analog thereof), an epitope that binds to an antibody (or functional fragment thereof), a carbohydrate that binds to a lectin, or the like. Thus, a ternary complex inhibitor can be a ligand (or other) moiety that is capable of binding to a receptor (or other molecule) to form a ligand-receptor complex that inhibits ternary complex formation. Further examples of moieties that can be used as ternary complex inhibitors include base modifications and nucleotide analogs described in Turcatti et al. *Nucl. Acids. Res.* 36(4) e25 (2008).

As used herein, the term "type" is used to identify molecules that share the same chemical structure. For example, a mixture of nucleotides can include several dCTP molecules. The dCTP molecules will be understood to be the same type as each other, but a different type compared to dATP, dGTP, dTTP etc. Similarly, individual DNA molecules that have the same sequence of nucleotides are the same type, whereas DNA molecules with different sequences are different types. The term "type" can also identify moieties that share the same chemical structure. For example, the cytosine bases in a template nucleic acid will be understood to be the same type of base as each other independent of their position in the template sequence.

The embodiments set forth below and recited in the claims can be understood in view of the above definitions.

The present disclosure provides a method for identifying a nucleotide in a template nucleic acid. The method can include steps of (a) providing a plurality of primer-template nucleic acid hybrids, wherein the primers have an extendable 3' end; (b) contacting the plurality with: (i) blocked nucleotides to produce a first subset of the primer-template nucleic acid hybrids that include a blocked nucleotide at the 3' end, and (ii) a ternary complex inhibitor to produce a second subset of the primer-template nucleic acid hybrids that include a ternary complex inhibitor; (c) forming ternary complexes that each include a polymerase, a primer-template nucleic acid hybrid of the first subset, and a cognate nucleotide; and (d) detecting the ternary complexes, thereby identifying a nucleotide in the template nucleic acid. Optionally the blocked nucleotides can be reversibly terminated nucleotides.

A method of the present disclosure can include a primer modification process, whereby a nucleotide or other moiety is added to the primer component of a primer-template nucleic acid hybrid. The primer modification process can be used to prepare the primer-template nucleic acid hybrid for an examination process, whereby the next base of the template nucleic acid is detected. Optionally, examination is performed to detect a ternary complex that forms between the next base of the primer-template nucleic acid hybrid, a polymerase and a cognate nucleotide for the next base (i.e. the cognate nucleotide also being referred to as the next correct nucleotide). Further details regarding the examination process are set forth below.

Returning to the primer modification process, a modification that results in extension of the primer with one or more nucleotides can be used to change the position of the template nucleic acid that will be examined next. For example, extension can be used to add one nucleotide to the primer, thereby shifting the position for ternary complex formation by one template position. The template nucleic acid can be sequenced using repeated cycles of examining ternary complex formation at the end of the primer (i.e. at the next template base) and then extending the primer to shift the position of examination.

Failure to extend a primer during a primer modification process can lead to loss of accuracy, for example, due to confusion as to which position of the template is actually being examined at any given cycle, or reduced read length, for example, when extension is incapable of proceeding. When detecting an ensemble of primer-template nucleic acid hybrids, even relatively minor extension inefficiencies can lead to phasing problems that will adversely impact read accuracy and read length.

A primer modification process that is used in a method set forth herein can provide a means to mitigate against artifacts that would otherwise arise from extension failures and inefficiencies. In particular embodiments, the primer modification process can include at least two steps: (i) contacting a primer-template nucleic acid hybrid and polymerase with a reversibly terminated nucleotide to produce a first subset of the primer-template nucleic acid hybrids that include a reversibly terminated nucleotide at the 3' end, and (ii) contacting a primer-template nucleic acid hybrid and polymerase with a ternary complex inhibitor to produce a second subset of the primer-template nucleic acid hybrids that include a ternary complex inhibitor. Step (i) can provide the benefit of extending the primer such that the first subset of primer-template nucleic acid hybrids can continue to participate in providing sequence information. For example, the reversibly terminated nucleotide used in step (i) can be selected to accommodate subsequent formation and examination of a ternary complex for the reversibly terminated primer. Step (ii) can provide the benefit of capping primers to prevent them from participating in formation of ternary complexes during subsequent examination steps. This capping can reduce phasing, increase accuracy of base calling and extend sequencing read lengths. Generally, step (i) will be performed prior to step (ii). However, the steps can be performed simultaneously or in opposite order. When performed serially, one of the steps can immediately follow the other, one of the steps can start prior to the previous step ending, or another step can intervene between the two steps.

When extension is carried out with reversibly terminated nucleotides, a particularly useful capping chemistry will be selective for the 3' end of non-extended primers compared to the 3' end of extended primers. For example, capping chemistry can be reactive to the 3' end of non-blocked primers and inert to modifying blocked primers. In this configuration, capping can function to clean up an extension step. Chemistry that uses enzymes that are specific for native 3' ends of primers are particularly useful, including for example, ligases and polymerases. A capping procedure that is more efficient at modifying native 3' primer ends, as compared to blocked primers is beneficial for many applications.

In particular embodiments, a ternary complex inhibitor is used to cap a primer. Any of a variety of moieties can be added to a primer to hinder or prevent subsequent formation of ternary complex at the 3' end of the primer. For example, a primer can be modified to have an oligonucleotide moiety attached thereto. An oligonucleotide moiety can have a length that is at least as long as the region of the template that was single stranded prior to the primer being modified. For example, the oligonucleotide moiety can extend from the 3' end of the primer to the 5' end of the template. In another example, the oligonucleotide moiety can extend from the 3' end of the primer to the 5' end of a double stranded region that is adjacent to the template region. In this example, the 5' end of the double stranded region forms a boundary to the template region. Other boundaries can be present such as a bound protein, chemical modification, point of attachment to a solid support or the like. An oligonucleotide moiety can have a length that prevents ternary complex from binding to the template between the primer and the boundary. Ternary complex inhibition can result when the entirety of the template region is double stranded, thereby removing single stranded locations where ternary complex can form.

Optionally, a primer can be attached to an oligonucleotide moiety as a result of ligase catalyzed attachment of the 5' end of the oligonucleotide to the 3' end of the primer or as a result of polymerase catalyzed extension of the primer with a series of nucleotides. Ligases, polymerases and other enzymes that modify primers can be useful. However, chemical techniques can also be useful for modifying a primer in a method set forth herein. An oligonucleotide moiety that is attached to a primer can be composed of entirely natural nucleotides that form natural Watson-Crick base pairs with the template. Alternatively, the oligonucleotide can include one or more non-natural nucleotide analogs. These analogs can be selected for their ability to form base pairs with the template, but analogs that do not pair with the template can also be used. Similarly, natural nucleotides can be present at positions in the oligonucleotide moiety that form a mismatch that disrupts base pairing between the oligonucleotide and template. A particularly useful position for a mismatch or non-natural nucleotide analog is at the 3' end of the oligonucleotide moiety where it can function to hinder or preclude subsequent ternary complex formation.

Another example of a useful moiety that can be added to a primer to hinder or prevent subsequent formation of ternary complex at the 3' end of the primer is a single nucleotide (e.g. a natural nucleotide or non-natural nucleotide analog). For example, a mismatched nucleotide can be attached to the 3' end of the primer to prevent ternary complex formation. Particularly useful mismatches and polymerases that are affected in their ability to recognize the mismatches are set forth in Kwok et al., *Nucleic Acids Res.* 18(4): 999-1005 (1990), which is incorporated herein by reference. A mismatched nucleotide can be present at the 3' end of a primer, having been introduced via an oligonucleotide moiety that was added to a primer. In some embodiments, a series of two or more mismatched nucleotides can be present at or near the 3' end of a primer to achieve inhibition of ternary complex formation. Whether or not a nucleotide that is added to the 3' end of a primer is matched with the template, the nucleotide can include an exogenous moiety that functions as a ternary complex inhibitor. The exogenous moiety can have a steric blocking effect, whereby polymerase, nucleotide or both are blocked from forming ternary complex. The moiety can have other effects on ternary complex formation including, but not limited to, charge repulsion of the polymerase or cognate nucleotide, perturbation of the structure of the primer-template nucleic acid hybrid, polarity that repels the polymerase or cognate nucleotide, or the like.

Particularly useful moieties include, but are not limited to, biotin or other ligands that can hinder or prevent ternary complex formation due to their presence at the 3' end or due to interactions with streptavidin or other receptor that in turn prevents ternary complex formation. Other ligand-receptor pairs include, but are not limited to, an antibody (or functional fragment thereof such as a Fab or ScFv) and epitope; or a carbohydrate and a lectin; or binding partners set forth herein in the context of a secondary label. An advantage of using a ligand-receptor as a primer cap is that the ligand need not inhibit ternary complex formation until it becomes bound to a receptor. For example, a nucleotide that is attached to a ligand can bind to a polymerase and primer-template nucleic acid to form a ternary complex and the nucleotide can be incorporated in the primer to position the ligand at the 3' end of the primer. The receptor can then be bound to the ligand at the 3' end of the primer to inhibit formation of a ternary complex at the 3' end of the primer.

A primer can be capped with a moiety that inhibits detection of ternary complex even if the ternary complex is present. For example, when using luminescent labels to detect ternary complex formation, the cap can be a quencher that reduces or prevents signal from the luminescent label. By way of more specific example, a primer can be capped with a quenching moiety and a ternary complex can be formed between the capped primer, a polymerase and a luminescently labeled nucleotide. The luminescently labeled nucleotide can be prevented from producing a luminescent signal due to proximity of the quencher and luminescent label. Another moiety that can be used to inhibit detection of a ternary complex without necessarily inhibiting formation of the ternary complex is a member of a FRET pair that can be used for a ternary complex that is labeled with the other member of the FRET pair. The resulting shift in signal arising from the FRET phenomena can effectively reduce expected signal and thus produce an apparent inhibition of signal that would have arisen from an uncapped primer. In the case of FRET, the shifted signal can be detected to identify the presence of a capped primer. In some cases, the shifted FRET signal can be quantified to quantify the capped primer in a sample that is being examined. Other moieties that quench or modify signals from particular labels can be used as capping moieties when the particular labels are to be used for detecting ternary complexes.

In some embodiments, a primer modification process can be used to crosslink a polymerase to the 3' end of a non-extended primer. Conditions can be used to selectively retain polymerase at the 3' end of a primer having a native 3' hydroxyl moiety while removing polymerase from primers having a reversible terminator at the 3' end. The retained polymerase can be crosslinked to the primed-template nucleic acid hybrid and inhibited from subsequently binding to nucleotides to form ternary complex. Inhibition can be the result of denaturing the retained polymerase, crosslinking at the nucleotide binding site of the polymerase or other chemical or photochemical modifications known in the art for inactivating polymerase.

A plurality of primer-template nucleic acid hybrids that is made or used in accordance with the teachings herein can include a first subset of species having a reversibly terminated primer and a second subset of species having a cap such as a ternary complex inhibitor moiety. The number of primer-template nucleic acid hybrids in the first subset can be less than 99%, 90%, 80%, 70%, 60% or 51% of the plurality of primer-template nucleic acid hybrids. Alternatively or additionally, the number of primer-template nucleic acid hybrids in the first subset can be at least 50%, 60%, 70%, 80%, 90% or 99% of the plurality of primer-template nucleic acid hybrids. In some embodiments, the number of primer-template nucleic acid hybrids in the second subset is at most 1%, 10%, 20%, 30%, 40%, 50% or more of the plurality of primer-template nucleic acid hybrids. Alternatively or additionally, the number of primer-template nucleic acid hybrids in the second subset can be at least 50%, 40%, 30%, 20%, 10%, 1%, or less of the plurality of primer-template nucleic acid hybrids. Optionally, the second subset of primer-template nucleic acid hybrids consists essentially of one primer-template nucleic acid hybrid. In each of the above examples, the plurality of primer-template nucleic acid hybrids can be attached to a solid support, for example, being present at a particular feature of a nucleic acid array.

In sequencing embodiments, the relative number of primer-template nucleic acid hybrids in the first and second subsets can change as sequencing proceeds. In such cases sequencing can be allowed to proceed until a particular threshold population size is reached for one or both subsets. The threshold can be the same as those set forth above or the threshold can differ to suit a particular use of the methods. Alternatively, sequencing can proceed for a predetermined number of cycles or until a threshold for a different characteristic is achieved, such as acquiring adequate sequence information to make an identification or until signal-to-noise degrades to a particular level.

A first and second subset of primer-template nucleic acid hybrids can differ in other ways. Typically, the primers of the first subset (e.g. primers extended by addition of reversibly terminated nucleotides) will be the same length as each other. This is generally advantageous for providing uniform phase when detecting the next base of the template nucleic acids in an ensemble. However, the primers of the second subset (e.g. primers having ternary complex inhibitors) can differ in length compared to each other. Such a population can result when the species in the population arose from capping at different cycles of a sequencing method. Optionally, the primers of the second subset are shorter than the primers of the first subset. Alternatively, the primers of the second subset can be longer than the primers of the first subset.

In particular embodiments, a primer modification process can mitigate against artifacts arising from extension failures and inefficiencies by removing or degrading non-extended primers. For example, the primer modification process can include at least two steps: (i) contacting a primer-template nucleic acid hybrid and polymerase with a reversibly terminated nucleotide to produce a first subset of the primer-template nucleic acid hybrids that include a reversibly terminated nucleotide at the 3' end, and (ii) contacting a primer-template nucleic acid hybrid with an agent that removes or degrades primers, thereby producing a second subset that includes template nucleic acids that lack a functional primer. Step (i) can provide the benefit of extending the primer such that the first subset of primer-template nucleic acid hybrids can continue to participate in providing sequence information. Step (ii) can provide the benefit of preventing non-extended primers from participating in formation of ternary complexes during subsequent examination steps. Absence of non-extended primers can reduce phasing, increase accuracy of base calling and extend sequencing read lengths. Generally, step (i) will be performed prior to step (ii). However, the steps can be performed simultaneously or in opposite order. When performed serially, one of the steps can immediately follow the other, one of the steps can start prior to the previous step ending, or another step can intervene between the two steps.

In particular embodiments, reagents that are used to degrade a non-extended primer are selective for primers that lack a blocking moiety, such as a reversible terminator moiety, that is present in extended primers. For example, primer degradation can be carried out using an exonuclease or chemical agent that is active in degrading primers that lack a blocking moiety at the 3' end (e.g. primers that have not been extended by adding a blocked nucleotide) but inhibited by the presence of a blocking moiety on other primers (e.g. primers that have been extended to incorporate a blocked nucleotide at the 3' end). A 3' to 5' exonucleases can be particularly useful, examples of which include, but are not limited to, polymerases having 3' exonuclease activity, Exo III, or Exo VII. Optionally, the 3' end of the template component of a primed-template nucleic acid hybrid can be blocked, for example, via attachment to a solid support or via presence of a blocking moiety, to prevent unwanted degradation of the template. As a further option the 5' end of the primer and/or template can be blocked to prevent unwanted degradation.

A plurality of template nucleic acids can include a first subset of species hybridized to a reversibly terminated primer and a second subset of species having no primer, for example, due to the primer having been removed or degraded. The number of primer-template nucleic acid hybrids in the first subset can be less than 99%, 90%, 80%, 70%, 60% or 51% of the plurality of template nucleic acids. Alternatively or additionally, the number of primer-template nucleic acid hybrids in the first subset can be at least 50%, 60%, 70%, 80%, 90% or 99% of the plurality of template nucleic acids. In some embodiments, the number of template nucleic acids in the second subset is at most 1%, 10%, 20%, 30%, 40%, 50% or more of the plurality of template nucleic acids. Alternatively or additionally, the number of template nucleic acids in the second subset can be less than 50%, 40%, 30%, 20%, 10%, 1%, or less of the plurality of template nucleic acids. In each of the above examples, the plurality of template nucleic acids can be attached to a solid support, for example, being present at a particular feature of a nucleic acid array.

A primer modification process used in a method set forth herein need not use a labeled polymerase. For example, a polymerase that is used for an extension step or for a capping step need not be attached to an exogenous label (e.g. covalently or otherwise). Alternatively, a polymerase that is used for primer extension or capping can include an exogenous label, for example, a label that was used in a previous examination step.

Typically, a reversibly terminated nucleotide that is added to a primer in a method set forth herein does not have an exogenous label. This is because the extended primer need not be detected in a method set forth herein. However, if desired, one or more types of reversibly terminated nucleotides used in a method set forth herein can be detected, for example, via exogenous labels attached to the nucleotides. Exemplary reversible terminator moieties, methods for incorporating them into primers and methods for modifying the primers for further extension (often referred to as 'deblocking') are set forth in U.S. Pat. Nos. 7,544,794; 7,956,171; 8,034,923; 8,071,755; 8,808,989; or 9,399,798. Further examples are set forth in Bentley et al., *Nature* 456:53-59 (2008), WO 04/018497; U.S. Pat. No. 7,057,026; WO 91/06678; WO 07/123744; U.S. Pat. Nos. 7,329,492; 7,211,414; 7,315,019; 7,405,281, and US 2008/0108082, each of which is incorporated herein by reference.

Similarly, a ternary complex inhibitor, or other primer cap that is added to a primer in a method set forth herein, need not have an exogenous label. This is because a primer-template nucleic acid hybrid that includes a cap, such as a ternary complex inhibitor, need not be detected in a method set forth herein. However, if desired, one or more types of ternary complex inhibitors, or other caps used in a method set forth herein, can be detected, for example, via exogenous labels attached to the cap or ternary complex inhibitor.

A primer capping process can be carried out simultaneously with a primer extension process or the two processes can be separated by other processes set forth herein. For example, primer capping can occur immediately after primer extension. In another example, examination can be carried out between the primer extension process and the primer capping process. In some embodiments, primer capping can occur simultaneously with examination (e.g. primer capping reagents can be delivered to a reaction vessel along with reagents for forming a ternary complex).

A method of this disclosure can include an examination step wherein ternary complex is formed and detected. Embodiments of the methods exploit the specificity with which a polymerase can form a stabilized ternary complex with a primer-template nucleic acid hybrid and a next correct nucleotide. The next correct nucleotide can be non-covalently bound to the stabilized ternary complex, interacting with the other members of the complex solely via non-covalent interactions. Useful methods and compositions for forming a stabilized ternary complex are set forth in further detail below and in commonly owned U.S. Pat. App. Pub. No. 2017/0022553 A1 or U.S. patent application Ser. No. 15/677,870, published as US Pat. App. Pub. No. 2018/0044727 A1; US Pat. App. Pub. No. 2018/0187245 A1, which claims priority to U.S. Pat. App. Ser. No. 62/440,624;

or US Pat. App. Pub. No. 2018/0208983 A1, which claims priority to U.S. Pat. App. Ser. No. 62/450,397, each of which is incorporated herein by reference.

Typically, examination is carried out separately and discretely from primer modification, for example, due to a reagent exchange or wash that intervenes examination and modification. Alternatively, examination and one or more primer modification steps can occur in the same mixture in some embodiments. For example, examination and primer blocking can occur in the same mixture. Alternatively or additionally, examination and primer capping can occur in the same mixture.

While a ternary complex can form between a polymerase, primer-template nucleic acid hybrid and next correct nucleotide in the absence of certain catalytic metal ions (e.g., $Mg^{2+}$), chemical addition of the nucleotide is inhibited in the absence of the catalytic metal ions. Low or deficient levels of catalytic metal ions, causes non-covalent sequestration of the next correct nucleotide in a stabilized ternary complex. Other methods disclosed herein also can be used to produce a stabilized ternary complex.

Optionally, a stabilized ternary complex can be formed when the primer of the primer-template nucleic acid hybrid includes a blocking moiety (e.g. a reversible terminator moiety) that precludes enzymatic incorporation of an incoming nucleotide into the primer. The interaction can take place in the presence of stabilizers, whereby the polymerase-nucleic acid interaction is stabilized in the presence of the next correct nucleotide. The primer of the primer-template nucleic acid hybrid optionally can be either an extendible primer, or a primer blocked from extension at its 3'-end (e.g., blocking can be achieved by the presence of a reversible terminator moiety on the 3'-end of the primer). The primer-template nucleic acid hybrid, the polymerase and the cognate nucleotide are capable of forming a stabilized ternary complex when the base of the cognate nucleotide is complementary to the next base of the primer-template nucleic acid hybrid.

As set forth above, conditions that favor or stabilize a ternary complex can be provided by the presence of a blocking group that precludes enzymatic incorporation of an incoming nucleotide into the primer (e.g. a reversible terminator moiety on the 3' nucleotide of the primer) or by the absence of a catalytic metal ion. Other useful conditions include the presence of a ternary complex stabilizing agent such as a non-catalytic ion (e.g., a divalent or trivalent non-catalytic metal ion) that inhibits nucleotide incorporation or polymerization. Non-catalytic metal ions include, but are not limited to, calcium, strontium, scandium, titanium, vanadium, chromium, iron, cobalt, nickel, copper, zinc, gallium, germanium, arsenic, selenium, rhodium, europium, and terbium ions. Optionally, conditions that disfavor or destabilize binary complexes (i.e. complexes between polymerase and primed nucleic acid but lacking cognate nucleotide) are provided by the presence of one or more monovalent cations and/or glutamate anions. As a further option, a polymerase engineered to prevent catalytic activity or to prevent propensity for binary complex formation can be used.

In particular embodiments, a ternary complex is stabilized by the presence of $Li^+$, betaine or both. For example, reagents and techniques set forth in U.S. patent application Ser. No. 16/355,361 (which is incorporated herein by reference) can be used. Immiscible fluids can also be used to stabilize a ternary complex, including for example, as set forth in U.S. patent application Ser. No. 16/164,417, which is incorporated herein by reference.

Ternary complex stabilization conditions can be further formulated to accentuate the difference in affinity of polymerase toward primer-template nucleic acid hybrids in the presence of different nucleotides, for example, by destabilizing binary complexes. Optionally, the conditions cause differential affinity of the polymerase for the primer-template in the presence of different nucleotides. By way of example, the conditions include, but are not limited to, high salt and glutamate ions. For example, the salt may dissolve in aqueous solution to yield a monovalent cation, such as a monovalent metal cation (e.g., sodium ion or potassium ion). Optionally, the salt that provides the monovalent cations (e.g., monovalent metal cations) further provides glutamate ions. Optionally, the source of glutamate ions can be potassium glutamate. In some instances, the concentrations of potassium glutamate that can be used to alter polymerase affinity of the primer-template hybrid extend from 10 mM to 1.6 M of potassium glutamate, or any amount in between 10 mM and 1.6 M. As indicated above, high salt refers to a concentration of salt from 50 mM to 1.5 M salt.

It will be understood that options set forth herein for stabilizing a ternary complex need not be mutually exclusive and instead can be used in various combinations. For example, a ternary complex can be stabilized by one or a combination of means including, but not limited to, cross-linking of the polymerase domains, crosslinking of the polymerase to the nucleic acid, polymerase mutations that stabilize the ternary complex, allosteric inhibition by small molecules, uncompetitive inhibitors, competitive inhibitors, non-competitive inhibitors, absence of catalytic metal ions, presence of a blocking moiety on the primer, and other means set forth herein.

A stabilized ternary complex can include a native nucleotide, nucleotide analog or modified nucleotide as desired to suit a particular application or configuration of the methods. Optionally, a nucleotide analog has a nitrogenous base, five-carbon sugar, and phosphate group, wherein any moiety of the nucleotide may be modified, removed and/or replaced as compared to a native nucleotide. Nucleotide analogs may be non-incorporable nucleotides (i.e. nucleotides that are incapable of reacting with the 3' oxygen of a primer to form a covalent linkage). Such nucleotides that are incapable of incorporation include, for example, monophosphate and diphosphate nucleotides. In another example, the nucleotide may contain modification(s) to the triphosphate group that make the nucleotide non-incorporable. Examples of non-incorporable nucleotides may be found in U.S. Pat. No. 7,482,120, which is incorporated by reference herein. In some embodiments, non-incorporable nucleotides may be subsequently modified to become incorporable. Non-incorporable nucleotide analogs include, but are not limited to, alpha-phosphate modified nucleotides, alpha-beta nucleotide analogs, beta-phosphate modified nucleotides, beta-gamma nucleotide analogs, gamma-phosphate modified nucleotides, or caged nucleotides. Examples of nucleotide analogs are described in U.S. Pat. No. 8,071,755, which is incorporated by reference herein.

Nucleotide analogs that participate in stabilized ternary complexes can include terminators that reversibly prevent subsequent nucleotide incorporation at the 3'-end of the primer after the analog has been incorporated into the primer. For example, U.S. Pat. Nos. 7,544,794 and 8,034,923 (the disclosures of these patents are incorporated herein by reference) describe reversible terminators in which the 3'-OH group is replaced by a 3'-$ONH_2$ moiety. Another type of reversible terminator is linked to the nitrogenous base of a nucleotide as set forth, for example, in U.S. Pat. No.

8,808,989 (the disclosure of which is incorporated herein by reference). Other reversible terminators that similarly can be used in connection with the methods described herein include those described in references cited elsewhere herein or in U.S. Pat. Nos. 7,956,171, 8,071,755, and 9,399,798 (the disclosures of these U.S. patents are incorporated herein by reference). In certain embodiments, a reversible terminator moiety can be modified or removed from a primer, in a process known as "deblocking," allowing for subsequent nucleotide incorporation. Compositions and methods for deblocking are set forth in references cited herein in the context of reversible terminators.

Nucleotide analogs that participate in stabilized ternary complexes can include ternary complex inhibitors that prevent subsequent ternary complex formation at the 3'-end of the primer after the analog has been incorporated into the primer. The nucleotide analogs can include an exogenous label, but nucleotide analogs used herein need not include a label.

Alternatively, nucleotide analogs irreversibly prevent nucleotide incorporation at the 3'-end of the primer to which they have been incorporated. Irreversible nucleotide analogs include 2', 3'-dideoxynucleotides (ddNTPs such as ddGTP, ddATP, ddTTP, ddCTP). Dideoxynucleotides lack the 3'-OH group of dNTPs that would otherwise participate in polymerase-mediated primer extension. Thus, the 3' position has a hydrogen moiety instead of the native hydroxyl moiety. Irreversibly terminated nucleotides can be particularly useful for genotyping applications or other applications where primer extension or sequential detection along a template nucleic acid is not desired.

In some embodiments, a nucleotide that participates in forming a ternary complex can include an exogenous label. Optionally, an exogenously labeled nucleotide can include a reversible or irreversible terminator moiety, an exogenously labeled nucleotide can be non-incorporable, an exogenously labeled nucleotide can lack blocking moieties, an exogenously labeled nucleotide can be incorporable or an exogenously labeled nucleotide can be both incorporable and non-terminated. Exogenously labeled nucleotides can be particularly useful when used to form a stabilized ternary complex with a non-labeled polymerase. Alternatively, an exogenous label on a nucleotide can provide one partner in a fluorescence resonance energy transfer (FRET) pair and an exogenous label on a polymerase can provide the second partner of the pair. As such, FRET detection can be used to identify a stabilized ternary complex that includes both partners. Alternatively, a nucleotide that participates in forming a ternary complex can lack exogenous labels (i.e. the nucleotide can be "non-labeled"). Optionally, a non-labeled nucleotide can include a reversible or irreversible terminator moiety, a non-labeled nucleotide can be non-incorporable, a non-labeled nucleotide can lack terminator moieties, a non-labeled nucleotide can be incorporable, or a non-labeled nucleotide can be both incorporable and non-terminated. Non-labeled nucleotides can be useful when a label on a polymerase is used to detect a stabilized ternary complex. Non-labeled nucleotides can also be useful in an extension step of a method set forth herein. It will be understood that absence of a moiety or function for a nucleotide refers to the nucleotide having no such function or moiety. It will also be understood that one or more of the functions or moieties set forth herein for a nucleotide, or analog thereof, or otherwise known in the art for a nucleotide, or analog thereof, can be specifically omitted in a method or composition set forth herein.

Optionally, a nucleotide (e.g. a native nucleotide or synthetic nucleotide analog) is present in a mixture during formation of a stabilized ternary complex. For example, at least 1, 2, 3, 4 or more nucleotide types can be present. Alternatively or additionally, at most 4, 3, 2, or 1 nucleotide types can be present. Similarly, one or more nucleotide types that are present can be complementary to at least 1, 2, 3 or 4 base types in a template nucleic acid. Alternatively or additionally, one or more nucleotide types that are present can be complementary to at most 4, 3, 2, or 1 base types in a template nucleic acid.

Any nucleotide modification that does not prevent participation in a ternary complex may be used in the methods disclosed herein. The nucleotide may be bound permanently or transiently to a polymerase. Optionally, a nucleotide analog is fused to a polymerase, for example, via a covalent linker. Optionally, a plurality of nucleotide analogs is fused to a plurality of polymerases, wherein each nucleotide analog is fused to a different polymerase. Optionally, a nucleotide that is present in a stabilized ternary complex is not the means by which the ternary complex is stabilized. Accordingly, any of a variety of other ternary complex stabilization methods may be combined in a reaction utilizing a nucleotide analog.

In particular embodiments, the primer strand of a primer-template nucleic acid hybrid molecule that is present in a stabilized ternary complex is chemically unchanged by a polymerase that is present during one or more steps of a method set forth herein. For example, the primer need not be extended by formation of a new phosphodiester bond, nor shortened by nucleolytic degradation during a step for forming a stabilized ternary complex, nor during a step for detecting the stabilized ternary complex. The primer strand of a primer-template hybrid molecule that is present in a stabilized ternary complex need not be chemically modified, for example, the primer need not be modified to include a ternary complex inhibitor moiety or other primer capping moiety.

A ternary complex that is made or used in accordance with the present disclosure may optionally include one or more exogenous label(s). The label can be attached to a component of the ternary complex (e.g. attached to the polymerase, template nucleic acid, primer and/or cognate nucleotide) prior to formation of the ternary complex. Exemplary attachments include covalent attachments or non-covalent attachments such as those set forth herein, in references cited herein or known in the art. In some embodiments, a labeled component is delivered in solution to a solid support that is attached to an unlabeled component, whereby the label is recruited to the solid support by virtue of forming a stabilized ternary complex. As such, the support-attached component can be detected or identified based on observation of the recruited label. Whether used in solution phase or on a solid support, exogenous labels can be useful for detecting a stabilized ternary complex or an individual component thereof, during an examination step. An exogenous label can remain attached to a component after the component dissociates from other components that had formed a stabilized ternary complex. Exemplary labels, methods for attaching labels and methods for using labeled components are set forth in commonly owned U.S. Pat. App. Pub. No. 2017/0022553 A1 or U.S. patent application Ser. No. 15/677,870, published as US Pat. App. Pub. No. 2018/0044727 A1; Ser. No. 15/851,383, published as US Pat. App. Pub. No. 2018/0187245 A1; Ser. No. 15/873,343, published as US Pat. App. Pub. No. 2018/0208983 A1; 62/450,397; or 62/506,759, each of which is incorporated herein by reference.

Examples of useful exogenous labels include, but are not limited to, radiolabel moieties, luminophore moieties, fluorophore moieties, quantum dot moieties, chromophore moieties, enzyme moieties, electromagnetic spin labeled moieties, nanoparticle light scattering moieties, and any of a variety of other signal generating moieties known in the art. Suitable enzyme moieties include, for example, horseradish peroxidase, alkaline phosphatase, beta-galactosidase, or acetylcholinesterase. Exemplary fluorophore moieties include, but are not limited to umbelliferone, fluorescein, isothiocyanate, rhodamine, tetramethyl rhodamine, eosin, green fluorescent protein, erythrosin, coumarin, methyl coumarin, pyrene, malachite green, stilbene, lucifer Yellow™, Cascade Blue™, Texas Red™, dansyl chloride, phycoerythrin, phycocyanin, fluorescent lanthanide complexes such as those including Europium and Terbium, Cy3, Cy5, Cy7, Alexa dyes and others known in the art such as those described in *Principles of Fluorescence Spectroscopy*, Joseph R. Lakowicz (Editor), Plenum Pub Corp, 2nd edition (July 1999) and the 6th Edition of *Molecular Probes Handbook* by Richard P. Hoagland.

A secondary label can be used in a method of the present disclosure. A secondary label is a binding moiety that can bind specifically to a partner moiety. For example, a ligand moiety can be attached to a polymerase, nucleic acid or nucleotide to allow detection via specific affinity for labeled receptor. A secondary label need not be detected in a method set forth herein. For example, a secondary label can be a moiety (e.g. a ligand) that is at the 3' end of a primer and that binds to a molecule (e.g. a receptor) such that the bound molecule inhibits ternary complex formation at the 3' end of the labeled primer. Exemplary pairs of binding moieties that can be used include, without limitation, antigen and immunoglobulin or active fragments thereof, such as FAbs; immunoglobulin and immunoglobulin (or active fragments, respectively); avidin and biotin, or analogs thereof having specificity for avidin; streptavidin and biotin, or analogs thereof having specificity for streptavidin; or carbohydrates and lectins. A particularly useful class of epitopes that can be attached to nucleotides or primers are peptides for which antibodies (or functional fragments thereof) can be raised to create a ternary complex inhibitor.

In some embodiments, the secondary label can be a chemically modifiable moiety. In this embodiment, labels having reactive functional groups can be incorporated into a stabilized ternary complex. Subsequently, the functional group can be covalently reacted with a primary label moiety. Suitable functional groups include, but are not limited to, amino groups, carboxy groups, maleimide groups, oxo groups and thiol groups. Functional groups used for click chemistry and related methods for their synthesis and use can also be useful. Useful click chemistry reagents and methods are set forth in U.S. Pat. Nos. 6,737,236; 7,375,234; 7,427,678 and 7,763,736, each of which is incorporated herein by reference.

In alternative embodiments, a ternary complex can lack exogenous labels. For example, a ternary complex and all components participating in the ternary complex (e.g. polymerase, template nucleic acid, primer and/or cognate nucleotide) can lack one, several or all of the exogenous labels described herein or in the above-incorporated references. In such embodiments, ternary complexes can be detected based on intrinsic properties of the stabilized ternary complex, such as mass, charge, intrinsic optical properties or the like. Exemplary methods for detecting non-labeled ternary complexes are set forth in commonly owned U.S. Pat. App. Pub. No. 2017/0022553 A1 PCT App. Ser. No. PCT/US16/68916, published as WO 2017/117243, or U.S. Pat. App. Ser. No. 62/375,379 or Ser. No. 15/677,870 (published as US Pat. App. Pub. No. 2018/0044727 A1), each of which is incorporated herein by reference.

Generally, detection can be achieved in an examination step by methods that perceive a property that is intrinsic to a ternary complex or a label moiety attached thereto. Exemplary properties upon which detection can be based include, but are not limited to, mass, electrical conductivity, energy absorbance, luminescence or the like. Detection of luminescence can be carried out using methods known in the art pertaining to nucleic acid arrays. A luminophore can be detected based on any of a variety of luminescence properties including, for example, emission wavelength, excitation wavelength, fluorescence resonance energy transfer (FRET) intensity, quenching, anisotropy or lifetime. Other detection techniques that can be used in a method set forth herein include, for example, mass spectrometry which can be used to perceive mass; surface plasmon resonance which can be used to perceive binding at a surface; absorbance which can be used to perceive the wavelength of the energy a label absorbs; calorimetry which can be used to perceive changes in temperature due to presence of a label; electrical conductance or impedance which can be used to perceive electrical properties of a label, or other known analytic techniques. Examples of reagents and conditions that can be used to create, manipulate and detect stabilized ternary complexes include, for example, those set forth in commonly owned U.S. Pat. App. Pub. No. 2017/0022553 A1; PCT App. Ser. No. PCT/US16/68916, published as WO 2017/117243; or U.S. patent application Ser. No. 15/677,870, published as US Pat. App. Pub. No. 2018/0044727 A1; U.S. paten application Ser. No. 15/581,383, published as US Pat. App. Pub. No. 2018/0187245 A1; U.S. patent application Ser. No. 15/873,343, published as US Pat. App. Pub. No. 2018/0208983 A1; U.S. Pat. App. Ser. Nos. 62/450,397 or 62/506,759, each of which is incorporated herein by reference.

Some embodiments of the methods set forth herein utilize two or more distinguishable signals to distinguish stabilized ternary complexes from each other and/or to distinguish one base type in a template nucleic acid from another base type. For example, two or more luminophores can be distinguished from each other based on unique optical properties such as unique wavelength for excitation or unique wavelength of emission. In particular embodiments, a method can distinguish different stabilized ternary complexes based on differences in luminescence intensity. For example, a first ternary complex can be detected in a condition where it emits less intensity than a second ternary complex. Such intensity scaling (sometimes called 'grey scaling') can exploit any distinguishable intensity difference. Exemplary differences include a particular stabilized ternary complex having an intensity that is at most 10%, 25%, 33%, 50%, 66%, or 75% compared to the intensity of another stabilized ternary complex that is to be detected.

Intensity differences can result from using different luminophores, for example, each having a different extinction coefficient (i.e. resulting in different excitation properties) and/or different luminescence quantum yield (i.e. resulting in different emission properties). Alternatively, the same luminophore type can be used but can be present in different amounts. For example, all members of a first population of ternary complexes can be labeled with a particular luminophore, whereas a second population has only half of its members labeled with the luminophore. In this example, the second population would be expected to produce half the signal of the first population. The second population can be produced, for example, by using a mixture of labeled nucleotides and unlabeled nucleotides (in contrast to the first population containing primarily labeled nucleotides). Similarly, the second population can be produced, for example, by using a mixture of labeled polymerases and unlabeled polymerases (in contrast to the first population containing primarily labeled polymerases). In an alternative labeling scheme, a first population of ternary complexes can include polymerase molecules that have multiple labels that produce a particular luminescent signal and a second population of ternary complexes can include polymerase molecules that each have only one of the labels that produces the luminescent signal.

In some embodiments, the examination step is carried out in a way that the identity of at least one nucleotide type is imputed, for example, as set forth in commonly owned U.S. Pat. No. 9,951,385 or U.S. patent application Ser. No. 15/922,787, granted as U.S. Pat. No. 10,161,003, each of which is incorporated herein by reference. Alternatively or additionally to using imputation, an examination step can use disambiguation to identify one or more nucleotide types, for example, as set forth in commonly owned U.S. Pat. No. 9,951,385 or U.S. patent application Ser. No. 15/922,787, granted as U.S. Pat. No. 10,161,003, each of which is incorporated herein by reference.

Any of a variety of polymerases can be used in a method or apparatus set forth herein, for example, to form a stabilized ternary complex or to carry out primer modification. Polymerases that may be used include naturally occurring polymerases and modified variations thereof, including, but not limited to, mutants, recombinants, fusions, genetic modifications, chemical modifications, synthetics, and analogs. Naturally occurring polymerases and modified variations thereof are not limited to polymerases that have the ability to catalyze a polymerization reaction. Optionally, the naturally occurring and/or modified variations thereof have the ability to catalyze a polymerization reaction in at least one condition that is not used during formation or examination of a stabilized ternary complex. Optionally, the naturally-occurring and/or modified variations that participate in stabilized ternary complexes have modified properties, for example, enhanced binding affinity to nucleic acids, reduced binding affinity to nucleic acids, enhanced binding affinity to nucleotides, reduced binding affinity to nucleotides, enhanced specificity for next correct nucleotides, reduced specificity for next correct nucleotides, reduced catalysis rates, catalytic inactivity etc. Mutant polymerases include, for example, polymerases wherein one or more amino acids are replaced with other amino acids, or insertions or deletions of one or more amino acids. Exemplary polymerase mutants that can be used to form a stabilized ternary complex include, for example, those set forth in U.S. paten application Ser. No. 15/866,353, published as US Pat. App. Pub. Nos. 2018/0155698 A1, or 2017/0314072, each of which is incorporated herein by reference.

Modified polymerases include polymerases that contain an exogenous label moiety (e.g., an exogenous fluorophore), which can be used to detect the polymerase. Optionally, the label moiety can be attached after the polymerase has been at least partially purified using protein isolation techniques. For example, the exogenous label moiety can be covalently linked to the polymerase using a free sulfhydryl or a free amine moiety of the polymerase. This can involve covalent linkage to the polymerase through the side chain of a cysteine residue, or through the free amino group of the N-terminus. An exogenous label moiety can also be attached to a polymerase via protein fusion. Exemplary label moieties that can be attached via protein fusion include, for example, green fluorescent protein (GFP), phycobiliproteins (e.g. phycocyanin and phycoerythrin) or wavelength-shifted variants of GFP or phycobiliproteins. In some embodiments, an exogenous label on a polymerase can function as a member of a FRET pair. The other member of the FRET pair can be an exogenous label that is attached to a nucleotide that binds to the polymerase in a stabilized ternary complex. As such, the stabilized ternary complex can be detected or identified via FRET.

Alternatively, a polymerase that participates in a stabilized ternary complex, or that is used to modify a primer need not be attached to an exogenous label. For example, the polymerase need not be covalently attached to an exogenous label. Instead, the polymerase can lack any label until it associates with a labeled nucleotide and/or labeled nucleic acid (e.g. labeled primer and/or labeled template).

Different activities of polymerases can be exploited in a method set forth herein. A polymerase can be useful, for example, in a primer modification process such as a primer extension step or primer capping step, examination step or combination thereof. The different activities can follow from differences in the structure (e.g. via natural activities, mutations or chemical modifications). Nevertheless, polymerase can be obtained from a variety of known sources and applied in accordance with the teachings set forth herein and recognized activities of polymerases. Useful DNA polymerases include, but are not limited to, bacterial DNA polymerases, eukaryotic DNA polymerases, archaeal DNA polymerases, viral DNA polymerases and phage DNA polymerases. Bacterial DNA polymerases include *E. coli* DNA polymerases I, II and III, IV and V, the Klenow fragment of *E. coli* DNA polymerase, *Clostridium stercorarium* (Cst) DNA polymerase, *Clostridium thermocellum* (Cth) DNA polymerase and *Sulfolobus solfataricus* (Sso) DNA polymerase. Eukaryotic DNA polymerases include DNA polymerases $\alpha$, $\beta$, $\gamma$, $\delta$, $\epsilon$, $\eta$, $\zeta$, $\lambda$, $\sigma$, $\mu$, and k, as well as the Rev1 polymerase (terminal deoxycytidyl transferase) and terminal deoxynucleotidyl transferase (TdT). Viral DNA polymerases include T4 DNA polymerase, phi-29 DNA polymerase, GA-1, phi-29-like DNA polymerases, PZA DNA polymerase, phi-15 DNA polymerase, Cpl DNA polymerase, Cpl DNA polymerase, T7 DNA polymerase, and T4 polymerase. Other useful DNA polymerases include thermostable and/or thermophilic DNA polymerases such as *Thermus aquaticus* (Taq) DNA polymerase, *Thermus filiformis* (Tfi) DNA polymerase, *Thermococcus zilligi* (Tzi) DNA polymerase, *Thermus thermophilus* (Tth) DNA polymerase, *Thermus flavusu* (Tfl) DNA polymerase, *Pyrococcus woesei* (Pwo) DNA polymerase, *Pyrococcus furiosus* (Pfu) DNA polymerase and Turbo Pfu DNA polymerase, *Thermococcus litoralis* (Tli) DNA polymerase, *Pyrococcus* sp. GB-D polymerase, *Thermotoga maritima* (Tma) DNA polymerase, *Bacillus stearothermophilus* (Bst) DNA polymerase, *Pyrococcus Kodakaraensis* (KOD) DNA polymerase, Pfx DNA polymerase, *Thermococcus* sp. JDF-3 (JDF-3) DNA polymerase, *Thermococcus gorgonarius* (Tgo) DNA polymerase, *Thermococcus acidophilium* DNA polymerase; *Sulfolobus acidocaldarius* DNA polymerase; *Thermococcus* sp. go N-7 DNA polymerase; *Pyrodictium occultum* DNA polymerase; *Methanococcus voltae* DNA polymerase; *Methanococcus thermoautotrophicum* DNA polymerase; *Methanococcus jannaschii* DNA polymerase; *Desulfurococcus* strain TOK DNA polymerase (D. Tok Pol); *Pyrococcus abyssi* DNA polymerase; *Pyrococcus horikoshii* DNA polymerase; *Pyrococcus islandicum* DNA polymerase; *Thermococcus fumicolans* DNA polymerase; *Aeropyrum pernix* DNA polymerase; and the heterodimeric DNA polymerase DP1/DP2. Engineered and modified polymerases also are useful in connection with the disclosed techniques. For example, modified versions of the extremely thermophilic marine archaea *Thermococcus* species 9° N (e.g., Therminator DNA polymerase from New England BioLabs Inc.; Ipswich, Mass.) can be used. Still other useful DNA polymerases, including the 3PDX polymerase are disclosed in U.S. Pat. No. 8,703,461, the disclosure of which is incorporated herein by reference.

Useful RNA polymerases include, but are not limited to, viral RNA polymerases such as T7 RNA polymerase, T3 polymerase, SP6 polymerase, and Kll polymerase; Eukaryotic RNA polymerases such as RNA polymerase I, RNA polymerase II, RNA polymerase III, RNA polymerase IV, and RNA polymerase V; and Archaea RNA polymerase.

Another useful type of polymerase is a reverse transcriptase. Exemplary reverse transcriptases include, but are not limited to, HIV-1 reverse transcriptase from human immunodeficiency virus type 1 (PDB 1HMV), HIV-2 reverse transcriptase from human immunodeficiency virus type 2, M-MLV reverse transcriptase from the Moloney murine leukemia virus, AMV reverse transcriptase from the avian myeloblastosis virus, and Telomerase reverse transcriptase that maintains the telomeres of eukaryotic chromosomes.

A polymerase having an intrinsic 3'-5' proofreading exonuclease activity can be useful for some embodiments. Polymerases that substantially lack 3'-5' proofreading exonuclease activity are also useful in some embodiments, for example, in most genotyping and sequencing embodiments. Absence of exonuclease activity can be a wild type characteristic or a characteristic imparted by a variant or engineered polymerase structure. For example, exo minus Klenow fragment is a mutated version of Klenow fragment that lacks 3'-5' proofreading exonuclease activity. Klenow fragment and its exo minus variant can be useful in a method or composition set forth herein.

Nucleic acids that are used in a method or composition herein can be DNA such as genomic DNA, synthetic DNA, amplified DNA, complementary DNA (cDNA) or the like. RNA can also be used such as mRNA, ribosomal RNA, tRNA or the like. Nucleic acid analogs can also be used as templates herein. Thus, template nucleic acids used herein can be derived from a biological source, synthetic source or amplification product. Primers used herein can be DNA, RNA or analogs thereof.

Particularly useful nucleic acid templates are genome fragments that each include a sequence identical to a portion of a genome. A population of genome fragments can cover all or part of the sequence of a particular genome. For example, a population of genome fragments can include sequences for at least 5%, 10%, 20%, 30%, 40%, 50%, 60%, 70%, 75%, 80%, 85%, 90%, 95% or 99% of a genome. A genome fragment can have, for example, a sequence that is substantially identical to at least about 25, 50, 70, 100, 200, 300, 400, 500, 600, 700, 800, 900 or 1000 or more contiguous nucleotides of a genome. Alternatively or additionally, a genome fragment can have a sequence that is substantially identical to no more than $1 \times 10^5$, $1 \times 10^4$, $1 \times 10^3$, 800, 600, 400, 200, 100, 75, 50 or 25 contiguous nucleotides of a genome. A genome fragment can be DNA, RNA, or an analog thereof.

Exemplary organisms from which nucleic acids can be derived include, for example, a mammal such as a rodent, mouse, rat, rabbit, guinea pig, ungulate, horse, sheep, pig, goat, cow, cat, dog, primate, human or non-human primate; a plant such as *Arabidopsis thaliana*, corn, sorghum, oat, wheat, rice, canola, or soybean; an algae such as *Chlamydomonas reinhardtii*; a nematode such as *Caenorhabditis elegans*; an insect such as *Drosophila melanogaster*, mosquito, fruit fly, honey bee or spider; a fish such as zebrafish; a reptile; an amphibian such as a frog or *Xenopus laevis*; a *Dictyostelium discoideum*; a fungi such as *Pneumocystis carinii, Takifugu rubripes*, yeast, *Saccharamoyces cerevisiae* or *Schizosaccharomyces pombe*; or a *plasmodium falciparum*. Nucleic acids can also be derived from a prokaryote such as a bacterium, *Escherichia coli, staphylococci* or *Mycoplasma pneumoniae*; an archae; a virus such as Hepatitis C virus or human immunodeficiency virus; or a viroid. Nucleic acids can be derived from a homogeneous culture or population of the above organisms or alternatively from a collection of several different organisms, for example, in a community or ecosystem. Nucleic acids can be isolated using methods known in the art including, for example, those described in Sambrook et al., *Molecular Cloning: A Laboratory Manual*, 3rd edition, Cold Spring Harbor Laboratory, New York (2001) or in Ausubel et al., *Current Protocols in Molecular Biology*, John Wiley and Sons, Baltimore, Md. (1998), each of which is incorporated herein by reference.

A template nucleic acid can be obtained from a preparative method such as genome isolation, genome fragmentation, gene cloning and/or amplification. The template can be obtained from an amplification technique such as polymerase chain reaction (PCR), rolling circle amplification (RCA), multiple displacement amplification (MDA) or the like. Exemplary methods for isolating, amplifying and fragmenting nucleic acids to produce templates for analysis on an array are set forth in U.S. Pat. No. 6,355,431 or 9,045,796, each of which is incorporated herein by reference. Amplification can also be carried out using a method set forth in Sambrook et al., *Molecular Cloning: A Laboratory Manual*, 3rd edition, Cold Spring Harbor Laboratory, New York (2001) or in Ausubel et al., *Current Protocols in Molecular Biology*, John Wiley and Sons, Baltimore, Md. (1998), each of which is incorporated herein by reference.

Examples of reagents and conditions that can be used for a polymerase-based primer extension step include, for example, those set forth in commonly owned U.S. Pat. App. Pub. No. 2017/0022553 A1 or U.S. patent application Ser. No. 15/677,870, published as US Pat. App. Pub. No. 2018/0044727 A1; U.S. patent application Ser. No. 15/851,383, published as US Pat. App. Pub. 2018/0187245 A1; or US Pat. App. Pub. No. 2018/0208983 A1, which claims priority to U.S. Pat App. Ser. Nos. 62/450,397 and 62/506,759, each of which is incorporated herein by reference. Other useful reagents and conditions for polymerase-based primer extension are set forth in Bentley et al., *Nature* 456:53-59 (2008), WO 04/018497; WO 91/06678; WO 07/123744; U.S. Pat. Nos. 7,057,026; 7,329,492; 7,211,414; 7,315,019 or 7,405,281, and US Pat. App. Pub. No. 2008/0108082 A1, each of which is incorporated herein by reference.

In particular embodiments, reagents that are used during a primer modification step (e.g. extending the primer via addition of a nucleotide or capping the primer via addition of a ternary complex inhibitor moiety) are removed from contact with the primer-template hybrid prior to a step of forming a stabilized ternary complex with the primer-template hybrid. For example, removal of a nucleotide mixture that was used for an extension step can be desirable when one or more types of nucleotides in the mixture would interfere with formation or detection of a ternary complex in a subsequent examination step. Similarly, it may be desirable to remove polymerases or cofactors that were used in a primer modification step so as to prevent unwanted catalytic activity during a subsequent examination step. Removal can be followed by a wash step, wherein an inert fluid is used to purge the primer-template hybrid of residual components of the reagent mixture used for primer modification.

A reagent removal or wash procedure can be performed between any of a variety of steps set forth herein. Such procedures can be used to remove one or more of the reagents that are present in a reaction vessel or on a solid support. For example, a reagent removal or wash step can be useful for separating a primer-template hybrid from other reagents that were contacted with the primer-template hybrid under ternary complex stabilizing conditions. In particular embodiments, separation of reagents is facilitated by attachment of a reagent of interest, such as a primer-template hybrid, to a solid support and removal of fluid from contact with the solid support. One or more of the reagents set forth herein can be attached to a solid support or provided in solution as desired to suit a particular use of the methods or apparatus set forth herein.

A reagent removal or wash procedure can be used to remove one or more reagents from interfering with examination of a mixture or from contaminating a second mixture that is to be formed on a substrate (or in a vessel) that had previously been in contact with the first mixture. For example, a primer-template nucleic acid hybrid can be contacted with a polymerase and at least one nucleotide type to form a first mixture under ternary complex stabilizing conditions, and the first mixture can be examined. Optionally, a wash can be carried out prior to detection in order to remove reagents that are not participating in formation of a stabilized ternary complex. Alternatively or additionally, a wash can be carried out after the detection step to remove one or more component of the first mixture from the primer-template hybrid. Then the primer-template hybrid can be contacted with a polymerase and at least one other nucleotide to form a second mixture under ternary complex stabilizing conditions, and the second mixture can be examined for ternary complex formation. As before, an optional wash can be carried out prior to the second examination to remove reagents that are not participating in formation of a stabilized ternary complex.

In particular embodiments, a primer capping step is carried out after primer extension. One or more of the reagents that were present in the primer extension step can be removed prior to introducing reagents for the primer capping step. For example, a primer-template nucleic acid hybrid that is attached to a solid support can be contacted with an extension mixture that includes polymerase(s) and nucleotide(s), the extension mixture can then be removed from the solid support, and then reagents for capping the primer can be delivered to the solid support. A wash fluid can be delivered to the solid support between the extension process and the capping process. This can help remove residual components of the extension mixture prior to delivering the capping reagents.

In alternate embodiments, reagents for primer extension and primer capping can be in simultaneous contact with each other. For example, a primer-template nucleic acid hybrid that is attached to a solid support can be contacted with a primer modification mixture that includes polymerase(s), nucleotide(s) having reversible terminator moieties (i.e. for extending the primer) and a ternary complex inhibitor moiety (i.e. for capping non-extended primers). The extension and capping reagents need not be delivered simultaneously to the solid support. Rather, the reagents can be delivered in a serial fashion such that they are simultaneously present after cumulative deliveries have been carried out. The extension and capping reagents can be removed prior to a subsequent step, such as an examination or deblocking step. A wash can optionally be employed to remove residual extension and capping reagents prior to a subsequent step.

Nucleotides present in an examination step may cause unwanted side reactions, such as nucleotide incorporation reactions, if carried over into a primer modification process, such as a primer extension process or primer capping process. Thus, a reagent removal or wash step can be employed prior to a primer modification step. Optionally, free nucleotides or other examination reagents may be modified or disabled, for example, by enzymes such as phosphatases, by chemical modification or by physical techniques.

Particular embodiments of the methods set forth herein include a step of forming a mixture that includes several components. For example, a mixture can be formed between a primer-template nucleic acid hybrid, a polymerase and one or more nucleotide types. The components of the mixture can be delivered to a vessel in any desired order or they can be delivered simultaneously. Furthermore, some of the components can be mixed with each other to form a first mixture that is subsequently contacted with other components to form a more complex mixture. Taking as an example, a step of forming a mixture that includes a primer-template nucleic acid hybrid, a polymerase and a plurality of different nucleotide types, it will be understood that the different nucleotide types in the plurality can be contacted with each other prior to being contacted with the primer-template nucleic acid hybrid. Alternatively, two or more of the nucleotide types can be delivered separately to the primer-template hybrid and/or the polymerase. As such, a first nucleotide type can be contacted with the primer-template hybrid prior to being contacted with a second nucleotide type. Alternatively or additionally, the first nucleotide type can be contacted with the polymerase prior to being contacted with a second nucleotide type.

A stabilized ternary complex, or a component that is capable of forming (i.e. participating in the formation of) a ternary complex, can be attached to a solid support. The solid support can be made from any of a variety of materials used for analytical biochemistry. Suitable materials may include glass, polymeric materials, silicon, quartz (fused silica), borofloat glass, silica, silica-based materials, carbon, metals, an optical fiber or bundle of optical fibers, sapphire, or plastic materials. The material can be selected based on properties desired for a particular use. For example, materials that are transparent to a desired wavelength of radiation are useful for analytical techniques that will utilize radiation of that wavelength. Conversely, it may be desirable to select a material that does not pass radiation of a certain wavelength (e.g. being opaque, absorptive or reflective). Other properties of a material that can be exploited are inertness or reactivity to certain reagents used in a downstream process, such as those set forth herein, or ease of manipulation, or low cost of manufacture.

A particularly useful solid support is a particle such as a bead or microsphere. Populations of beads can be used for attachment of populations of stabilized ternary complexes or components capable of forming the complexes (e.g. polymerases, templates, primers or nucleotides). In some embodiments, it may be useful to use a configuration whereby each bead has a single type of stabilized ternary complex or a single type of component capable of forming the complex. For example, an individual bead can be attached to a single type of ternary complex, a single type of primer-template nucleic acid hybrid, a single type of primer, a single type of template, a single type of polymerase or a single type of nucleotide. Alternatively, different types of components need not be separated on a bead-by-bead basis. As such, a single bead can bear multiple different types of ternary complexes, template nucleic acids, primers, primer-template nucleic acid hybrids and/or nucleotides. The composition of a bead can vary, depending for example, on the format, chemistry and/or method of attachment to be used. Exemplary bead compositions include solid supports, and chemical functionalities imparted thereto, used in protein and nucleic acid capture methods. Such compositions include, for example, plastics, ceramics, glass, polystyrene, melamine, methylstyrene, acrylic polymers, paramagnetic materials, thoria sol, carbon graphite, titanium dioxide, latex or cross-linked dextrans such as Sepharose™, cellulose, nylon, cross-linked micelles and Teflon™, as well as other materials set forth in "Microsphere Detection Guide" from Bangs Laboratories, Fishers Ind., which is incorporated herein by reference.

The geometry of a particle, such as a bead or microsphere, also can correspond to a wide variety of different forms and shapes. For example, a particle can be symmetrically shaped (e.g. spherical or cylindrical) or irregularly shaped (e.g. controlled pore glass). In addition, particles can be porous, thus increasing the surface area available for capture of ternary complexes or components thereof. Exemplary sizes for beads used herein can range from nanometers to millimeters or from about 10 nm-1 mm.

In particular embodiments, beads can be arrayed or otherwise spatially distinguished. Exemplary bead-based arrays that can be used include, without limitation, a BeadChip™ Array available from Illumina, Inc. (San Diego, Calif.) or arrays such as those described in U.S. Pat. Nos. 6,266,459; 6,355,431; 6,770,441; 6,859,570; or 7,622,294; or PCT Publication No. WO 00/63437, each of which is incorporated herein by reference. Beads can be located at discrete locations, such as wells, on a solid-phase support, whereby each location accommodates a single bead. Alternatively, discrete locations where beads reside can each include a plurality of beads as described, for example, in U.S. Pat. App. Pub. Nos. 2004/0263923 A1, 2004/0233485 A1, 2004/0132205 A1, or 2004/0125424 A1, each of which is incorporated herein by reference.

As will be recognized from the above bead array embodiments, a method of the present disclosure can be carried out in a multiplex format whereby multiple different types of nucleic acids are detected in parallel in a method set forth herein. Although it is also possible to serially process different types of nucleic acids using one or more steps of the methods set forth herein, parallel processing can provide cost savings, time savings and uniformity of conditions. An apparatus or method of the present disclosure can include at least 2, 10, 100, $1\times10^3$, $1\times10^4$, $1\times10^5$, $1\times10^6$, $1\times10^9$, or more different nucleic acids. Alternatively or additionally, an apparatus or method of the present disclosure can include at most $1\times10^9$, $1\times10^6$, $1\times10^5$, $1\times10^4$, $1\times10^3$, 100, 10, 2 or fewer, different nucleic acids. Accordingly, various reagents or products set forth herein as being useful in the apparatus or methods (e.g. primer-template nucleic acid hybrids or stabilized ternary complexes) can be multiplexed to have different types or species in these ranges. The different nucleic acids that are present in an array can be located at different features of the array. Thus, signals acquired from a feature will be indicative of a particular nucleic acid sequence present at the feature.

Further examples of commercially available arrays that can be used include, for example, an Affymetrix GeneChip™ array. A spotted array can also be used according to some embodiments. An exemplary spotted array is a CodeLink™ Array available from Amersham Biosciences. Another array that is useful is one that is manufactured using inkjet printing methods such as SurePrint™ Technology available from Agilent Technologies.

Other useful arrays include those that are used in nucleic acid sequencing applications. For example, arrays that are used to attach amplicons of genomic fragments (often referred to as clusters) can be particularly useful. Examples of nucleic acid sequencing arrays that can be used herein include those described in Bentley et al., Nature 456:53-59 (2008); PCT Pub. Nos. WO 91/06678; WO 04/018497 or WO 07/123744; U.S. Pat. Nos. 7,057,026; 7,211,414; 7,315,019; 7,329,492 or 7,405,281; or U.S. Pat. App. Pub. No. 2008/0108082, each of which is incorporated herein by reference.

A nucleic acid can be attached to a support in a way that provides detection at a single molecule level or at an ensemble level. For example, a plurality of different nucleic acids can be attached to a solid support in a way that an individual stabilized ternary complex that forms on one nucleic acid molecule on the support can be distinguished from all neighboring ternary complexes that form on the nucleic acid molecules of the support. As such, one or more different templates can be attached to a solid support in a format where each single molecule template is physically isolated and detected in a way that the single molecule is resolved from all other molecules on the solid support.

Alternatively, a method of the present disclosure can be carried out for one or more nucleic acid ensembles, an ensemble being a population of nucleic acids having a common template sequence. An ensemble can include, for example, at least 2, 10, 50, 100, 500, 1000 or more nucleic acids having a common template sequence. Alternatively or additionally, an ensemble can include at most 1000, 500, 100, 50, 10 or 2 nucleic acids having a common template sequence. An ensemble that is present at a feature of an array can be clonal such that substantially all of the nucleic acids at the feature have a common template sequence. However, a feature need not contain a clonal population of nucleic acids. Rather, a feature can include a mixed population of nucleic acids, wherein a particular template sequence is present in a majority of the nucleic acids. For example, a population of nucleic acids that are at a particular feature can include at least 51%, 60%, 75%, 90%, 95% or 99% or more species having a particular template sequence. A feature having a non-clonal population of nucleic acids can be detected under conditions that allow the population to be detected as an ensemble, whereby the total signal acquired from the feature represents an average of signals produced by the non-clonal population. So long as contaminating nucleic acids are present as a minority at a feature of interest, the average signal can provide a means to characterize the majority of template nucleic acids at the feature.

Cluster methods can be used to attach one or more ensembles to a solid support. As such, an array can have a plurality of ensembles, each of the ensembles being referred to as a cluster or array feature in that format. Clusters can be formed using methods known in the art such as bridge amplification or emulsion PCR. Useful bridge amplification methods are described, for example, in U.S. Pat. No. 5,641,658 or 7,115,400; or U.S. Patent Pub. Nos. 2002/0055100 A1; 2004/0002090 A1; 2004/0096853 A1; 2007/0128624 A1; or 2008/0009420 A1. Emulsion PCR methods include, for example, methods described in Dressman et al., *Proc. Natl. Acad. Sci. USA* 100:8817-8822 (2003), WO 05/010145, or U.S. Patent Pub. Nos. 2005/0130173 A1 or 2005/0064460 A1, each of which is incorporated herein by reference in its entirety. Another useful method for amplifying nucleic acids on a surface is rolling circle amplification (RCA), for example, as described in Lizardi et al., *Nat. Genet.* 19:225-232 (1998) or US 2007/0099208 A1, each of which is incorporated herein by reference.

In particular embodiments, a stabilized ternary complex, polymerase, primer, template, primer-template nucleic acid hybrid or nucleotide is attached to a flow cell surface or to a solid support in a flow cell. A flow cell allows convenient fluidic manipulation by passing solutions into and out of a fluidic chamber that contacts the support-bound, ternary complex. The flow cell also provides for detection of the fluidically manipulated components. For example, a detector can be positioned to detect signals from the solid support, such as signals from a label that is recruited to the solid support due to formation of a stabilized ternary complex. Exemplary flow cells that can be used are described, for example, in US Pat. App. Pub. No. 2010/0111768 A1, WO 05/065814 or US Pat. App. Pub. No. 2012/0270305 A1, each of which is incorporated herein by reference.

The present disclosure provides a method for sequencing a template nucleic acid. The method can include steps of (a) providing a plurality of primer-template nucleic acid hybrids, wherein the primers have an extendable 3' end; (b) contacting the plurality with: (i) reversibly terminated nucleotides to produce a first subset of the primer-template nucleic acid hybrids that include a reversibly terminated nucleotide at the 3' end, and (ii) a ternary complex inhibitor to produce a second subset of the primer-template nucleic acid hybrids that include a ternary complex inhibitor; (c) forming ternary complexes that each include a polymerase, a primer-template nucleic acid hybrid of the first subset, and a cognate nucleotide; (d) detecting the ternary complexes, thereby identifying a nucleotide in the template nucleic acid; (e) deblocking the reversibly terminated nucleotide at the 3' end of the primer-template nucleic acid hybrids in the first subset; and (f) repeating steps (b) through (e) to sequence template nucleic acids in the first subset.

A deblocking process when included in a method set forth herein can facilitate sequencing of a primer-template nucleic acid hybrid. The deblocking process can be used to convert a reversibly terminated primer into an extendable primer. Primer extension can then be used to move the site of ternary complex formation to a different location along the template nucleic acid. Repeated cycles of extension, examination and deblocking can be used to reveal the sequence of template nucleic acid. Each cycle reveals a subsequent base in the template nucleic acid. Exemplary reversible terminator moieties, methods for incorporating them into primers and methods for modifying the primers for further extension (often referred to as 'deblocking') are set forth in U.S. Pat. Nos. 7,427,673; 7,414,116; 7,544,794; 7,956,171; 8,034,923; 8,071,755; 8,808,989; or 9,399,798. Further examples are set forth in Bentley et al., *Nature* 456:53-59 (2008), WO 04/018497; U.S. Pat. No. 7,057,026; WO 91/06678; WO 07/123744; U.S. Pat. Nos. 7,329,492; 7,211,414; 7,315,019; 7,405,281, and US 2008/0108082, each of which is incorporated herein by reference.

A primer that has been modified to hinder or preclude subsequent formation of a ternary complex need not be treated to reverse the modification. Thus, a capped primer can remain capped throughout several cycles (and in some cases, all cycles) of a cyclical method such as a sequencing method. For example, a cyclical process can include a process for deblocking reversibly terminated primers and capped primers can be inert to the deblocking process.

A sequencing method can include multiple repetitions of cycles, or steps within cycles, set forth herein. For example, examination and primer modification steps can be repeated multiple times as can optional steps of deblocking primers or washing away unwanted reactants or products between various steps. Accordingly, a primer-template nucleic acid hybrid can be subjected to at least 2, 5, 10, 25, 50, 100, 150, 200 or more repeated cycles of a method set forth herein. Fewer cycles can be carried out when shorter read lengths are desired. As such, a primer-template nucleic acid hybrid can be subjected to at most 200, 150, 100, 50, 25, 10, 5 or 2 cycles of a method set forth herein.

In some embodiments, a sequencing method can be carried out for a predetermined number of repeated cycles. Alternatively, the cycles can be repeated until a particular empirically observed state is reached. For example, cycles can be repeated so long as signal is above an observable threshold, noise is below an observable threshold or signal-to-noise ratio is above an observable threshold.

In another example, cycles can be repeated so long as one or more ensembles (e.g. one or more clusters or features in an array) have a desired composition. As the one or more ensembles proceed through the sequencing cycles their composition may change. Considering a single ensemble as a set of template nucleic acids, a first subset of the templates that each have a primer with a reversibly terminated nucleotide at the 3' end may decrease in number as the cycles proceed, and a second subset of the template nucleic acids that each have a primer with a ternary complex inhibitor (or that each have no primer) may increase in number as the cycle proceeds. The sequencing method can continue until the first subset reaches a particular threshold and/or until the second subset reaches a particular threshold. More specifically, the cycles can be repeated until the number of primer-template nucleic acid hybrids in the first subset is less than 99%, 90%, 80%, 70%, 60% or 51% of the plurality of template nucleic acids being detected. Alternatively or additionally, the cycles can be repeated so long as the number of primer-template nucleic acid hybrids in the first subset is at least 50%, 60%, 70%, 80%, 90% or 99% of the plurality of template nucleic acids being detected. In some embodiments, the cycles can be repeated until the number of template nucleic acids in the second subset is at most 1%, 10%, 20%, 30%, 40%, 50% or more of the plurality of template nucleic acids being detected. Alternatively or additionally, the cycles can be repeated so long as the number of template nucleic acids in the second subset is at least 50%, 40%, 30%, 20%, 10%, or 1% of the plurality of template nucleic acids being detected.

It will be understood that not all of the steps set forth herein need to be repeated nor do repeated steps need to occur in the same order in each repetition.

The present disclosure further provides an apparatus that includes a plurality of primer-template nucleic acid hybrids, wherein a first subset of the primer-template nucleic acid hybrids has a blocked nucleotide at the 3' end of the primer, and wherein a second subset of the primer-template nucleic acid hybrids has a ternary complex inhibitor at the 3' end of the primer. Optionally, the blocked nucleotide can be a reversibly terminated nucleotide.

Optionally, a plurality of primer-template nucleic acid hybrids is attached to a solid support in an apparatus of the present disclosure. The solid support can include any of a variety of materials set forth herein including, for example, materials set forth herein in the context of nucleic acid arrays. The plurality of primer-template nucleic acid hybrids can be attached to a feature of the array and, optionally, the templates that are attached to the feature can have the same sequence. Any of a variety of reagents set forth herein can be attached to a solid support instead of the primer-template nucleic acid hybrids or, alternatively, in addition to attached primer-template nucleic acid hybrids. In particular embodiments, an apparatus of the present disclosure need not include attached reagents of any type.

In particular embodiments, an apparatus of the present disclosure includes a vessel, such as a manufactured vessel. The vessel can contain a plurality of primer-template nucleic acid hybrids along with other reagents or reaction products that participate in a method set forth herein. A particularly useful manufactured vessel is a flow cell, examples of which are set forth herein above.

An apparatus of the present disclosure can be a component of a larger system. For example, the system can include (a) an apparatus that includes a plurality of primer-template nucleic acid hybrids, wherein a first subset of the primer-template nucleic acid hybrids has a reversibly terminated nucleotide at the 3' end of the primer, and wherein a second subset of the primer-template nucleic acid hybrids has a ternary complex inhibitor at the 3' end of the primer; and (b) a detector configured to detect the plurality of primer-template nucleic acid hybrids. Optionally, the system can further include (c) a fluidic system including reservoirs containing polymerase and nucleotides, wherein the reservoirs are in fluidic communication with the plurality of primer-template nucleic acid hybrids.

A system of the present disclosure can be configured for detecting nucleic acids, for example, using methods set forth herein. For example, a system can be configured to produce and detect ternary complexes formed between a polymerase and a primer-template nucleic acid hybrid in the presence of nucleotides to identify one or more bases in a template nucleic acid sequence. Optionally, the system includes components and reagents for performing one or more steps set forth herein including, but not limited to, forming at least one stabilized ternary complex between a primer-template nucleic acid hybrid, polymerase and next correct nucleotide; detecting the stabilized ternary complex(es); modifying the primer of each primer-template hybrid, for example, via a primer capping or primer extension process; deblocking a reversibly terminated primer; and/or identifying a nucleotide, sequence of nucleotides, or series of base multiplets present in the template.

A system of the present disclosure can include a vessel, solid support or other apparatus for carrying out a nucleic acid detection method. For example, the system can include an array, flow cell, multi-well plate or other convenient apparatus. The apparatus can be removable, thereby allowing it to be placed into or removed from the system. As such, a system can be configured to process a plurality of apparatus (e.g. vessels or solid supports) sequentially or in parallel. The system can include a fluidic component having reservoirs for containing one or more of the reagents set forth herein (e.g. polymerase, primer, template nucleic acid, nucleotide(s) for ternary complex formation, nucleotides for primer extension, deblocking reagents, ternary complex inhibitors, or mixtures of such components). The fluidic system can be configured to deliver reagents to a vessel or solid support, for example, via channels or droplet transfer apparatus (e.g. electrowetting apparatus). Any of a variety of detection apparatus can be configured to detect the vessel or solid support where reagents interact. Examples include luminescence detectors, surface plasmon resonance detectors and others known in the art. Exemplary systems having fluidic and detection components that can be readily modified for use in a system herein include, but are not limited to, those set forth in US Pat. App. Pub. No. 2018/0280975 A1, which claims priority to U.S. Pat. App. Ser. No. 62/481,289; U.S. Pat. Nos. 8,241,573; 7,329,860 or 8,039,817; or US Pat. App. Pub. Nos. 2009/0272914 A1 or 2012/0270305 A1, each of which is incorporated herein by reference.

Optionally, a system of the present disclosure further includes a computer processing unit (CPU) that is configured to operate system components. The same or different CPU can interact with the system to acquire, store and process signals (e.g. signals detected in a method set forth herein). In particular embodiments, a CPU can be used to determine, from the signals, the identity of the nucleotide that is present at a particular location in a template nucleic acid. In some cases, the CPU will identify a sequence of nucleotides for the template from the signals that are detected.

A useful CPU can include one or more of a personal computer system, server computer system, thin client, thick client, hand-held or laptop device, multiprocessor system, microprocessor-based system, set top box, programmable consumer electronic, network PC, minicomputer system, mainframe computer system, smart phone, and distributed cloud computing environments that include any of the above systems or devices, and the like. The CPU can include one or more processors or processing units, a memory architecture that may include RAM and non-volatile memory. The memory architecture may further include removable/non-removable, volatile/non-volatile computer system storage media. Further, the memory architecture may include one or more readers for reading from and writing to a non-removable, non-volatile magnetic media, such as a hard drive, a magnetic disk drive for reading from and writing to a removable, non-volatile magnetic disk, and/or an optical disk drive for reading from or writing to a removable, non-volatile optical disk such as a CD-ROM or DVD-ROM. The CPU may also include a variety of computer system readable media. Such media may be any available media that is accessible by a cloud computing environment, such as volatile and non-volatile media, and removable and non-removable media.

The memory architecture may include at least one program product having at least one program module implemented as executable instructions that are configured to carry out one or more steps of a method set forth herein. For example, executable instructions may include an operating system, one or more application programs, other program modules, and program data. Generally, program modules may include routines, programs, objects, components, logic, data structures, and so on, that perform particular tasks set forth herein.

The components of a CPU may be coupled by an internal bus that may be implemented as one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

A CPU can optionally communicate with one or more external devices such as a keyboard, a pointing device (e.g.

a mouse), a display, such as a graphical user interface (GUI), or other device that facilitates interaction of a use with the nucleic acid detection system. Similarly, the CPU can communicate with other devices (e.g., via network card, modem, etc.). Such communication can occur via I/O interfaces. Still yet, a CPU of a system herein may communicate with one or more networks such as a local area network (LAN), a general wide area network (WAN), and/or a public network (e.g., the Internet) via a suitable network adapter.

This disclosure further provides kits for characterizing nucleic acids. Optionally, a kit can include reagents for carrying out one or more of the methods set forth herein. For example, a kit can include reagents for producing a stabilized ternary complex when mixed with one or more primer-template nucleic acid hybrid. In addition to the nucleotide mixtures the kit can include a polymerase that is capable of forming a stabilized ternary complex and/or a polymerase used for a primer modification step. Other reagents used for primer modification such as reversibly terminated nucleotides or ternary complex inhibitors can also be included in a kit. Reagents included in a kit, such as nucleotide(s), polymerase(s) or both, can include an exogenous label, for example, as set forth herein in the context of various methods.

Accordingly, any of the components or articles used in performing the methods set forth herein can be usefully packaged into a kit. For example, the kits can be packed to include some, many or all of the components or articles used in performing the methods set forth herein. Exemplary components include, for example, labeled nucleotides (e.g. extendible labeled nucleotides), polymerases (labeled or unlabeled), nucleotides having terminator moieties (e.g. unlabeled, reversibly terminated nucleotides), deblocking reagents, ternary complex inhibitors, and the like as set forth herein and in references cited herein. Any of such reagents can include, for example, some, many or all of the buffers, components and/or articles used for performing one or more of the subsequent steps for analysis of a primer-template nucleic acid hybrid. A kit need not include a primer or template nucleic acid. Rather, a user of the kit can provide one or more primer-template nucleic acid hybrids which are to be combined with components of the kit by the user.

One or more ancillary reagents also can be included in a kit. Such ancillary reagents can include any of the reagents exemplified above and/or other types of reagents useful in performing the methods set forth herein. Instructions can further be included in a kit. The instructions can include, for example, procedures for making any components or articles used in the methods set forth herein, performing one or more steps of any embodiment of the methods set forth herein and/or instructions for performing any of the subsequent analysis steps employing a primer-template nucleic acid hybrid.

In particular embodiments, a kit can include an apparatus set forth herein, such as a flow cell or solid support. Optionally, a kit includes a cartridge having reservoirs to contain the reagents and further having fluidic components for transferring reagents from the reservoirs to a detection instrument. For example, the fluidic components can be configured to transfer reagents to a flow cell where stabilized ternary complexes are detected. An exemplary fluidic cartridge that can be included in a kit (or system) of the present disclosure is described in U.S. patent application Ser. No. 15/922,661, published as US Pat. App. Pub. No. 2018/0280975 A1, which is incorporated herein by reference.

EXAMPLE I

Primer Capping Using Run-Off Primer Extension

This example demonstrates a technique for improving phasing when extending a population of primers. Phasing is improved by capping non-extended primers to prevent the capped primers from forming ternary complexes in subsequent examination steps.

A FORTEBIO® (Menlo Park, Calif.) Octet instrument employing biolayer interferometry to measure binding reactions at the surface of a fiber optic tip was used in a multi-well plate format. Template nucleic acids were attached to the streptavidin functionalized tips by incubating the tips in wells containing 5' biotinylated template nucleic acid at 37° C. for 5 minutes. Unbound template nucleic acid was removed by contacting the tips with 0.1M NaOH, blotting the tips dry and then washing the tips in PRE (50 mM KCl, 50 mM Tricine, pH 8.42, 0.1% Tween-80, 0.1% Hydroxylamine, 0.1 mM EDTA). Primer was hybridized to the tip-bound templates by incubation at 37° C. for 5 minutes in PRE.

The tips were then subjected to 30 primer extension cycles on the Octet instrument. Each cycle included steps of transferring the tips to the following reagents for the following incubation times: (1) PRE for 5 seconds; (2) RTS (PRE, 5 mM $MgCl_2$, 10 U/mL Therminator, 25 µM rtNTPs (reversibly terminated deoxynucleotides having aminooxy reversible terminator moiety on the 3' position)) for 10 seconds; (3) variable solution for 30 seconds; (4) ESB (1M GdSCN, 0.1 mM HEPES pH 7.5, 0.1% Tween-80, 0.1% Hydroxylamine, 2 mM EDTA) for 5 sec; (5) PRE for 5 sec; (6) CLV (0.25M Sodium Acetate pH 4.8, 0.7 M Sodium Nitrite) for 5 seconds; (7) PRE for 5 sec. The variable solutions contained the following reagents:

a) PRE b) PRE+10 u/ml Therminator c) PRE+10 u/ml Therminator+5 mg $Mg^{+2}$ d) PRE+10 u/ml Therminator+5 mg $Mg^{+2}$+100 µM dNTPs e) PRE+10 u/ml Therminator+5 mg $Mg^{+2}$+30 µM dNTPs f) PRE+10 u/ml Therminator+5 mg $Mg^{+2}$+10 µM dNTPs g) PRE+10 u/ml Therminator+5 mg $Mg^{+2}$+3 µM dNTPs h) PRE+10 u/ml Therminator+5 mg $Mg^{+2}$+1 µM dNTPs Following the Octet cycles, the primer strands were stripped from the tip-attached templates and incubated with capillary electrophoresis (CE) dye. The length of the primers was then determined using CE analysis. CE results were analyzed by checking each peak and recording the n and n−1 peak areas. Efficiency of primer extension was evaluated using the following formula: [(# of cycles)×(n/n−1 ratio)]÷[(# of cycles)×(n/n−1 ratio)+1].

The results are summarized in Table 1. The extended primers had CE mobility that was consistent with the expected length (n=59 nucleotides). The ratio of n/n−1 was lowest for the control conditions (i.e. a), b) and c)), and increased when nucleotides were present. The efficiency of full length extension also increased when all components necessary for primer extension were present.

TABLE 1

CE results

| Variable Condition | n (length) | n/n − 1 (Ratio of Areas) | Extension Efficiency |
|---|---|---|---|
| a) PRE | 58.99 | 12.26 | 99.73% |
| b) PRE + Pol | 59.03 | 13.54 | 99.75% |
| c) PRE + Pol + Mg | 59.05 | 16.15 | 99.79% |
| d) PRE + Pol + Mg + 100 µM dNTP | 59.03 | 30.77 | 99.89% |
| e) PRE + Pol + Mg + 30 µM dNTP | 59.05 | 34.30 | 99.90% |
| f) PRE + Pol + Mg + 10 µM dNTP | 58.99 | 36.04 | 99.91% |
| g) PRE + Pol + Mg + 3 µM dNTP | 59.02 | 34.41 | 99.90% |
| h) PRE + Pol + Mg +1 µM dNTP | 59.02 | 29.57 | 99.89% |

The results demonstrated that, following extension with reversibly terminated nucleotides (in RTS), further primer extension only occurred when all components necessary for primer extension were present (dNTPs, Therminator, and Mg). This shows that unblocked 3' ends remained and run off extension after RTS can be used to fully extend primers through the template region.

The fully extended primers are expected to be unavailable for formation of ternary complex during subsequent examination steps, leading to improved signal to noise, longer read lengths and higher sequencing accuracy.

Throughout this application various publications, patents and/or patent applications have been referenced. The disclosures of these documents in their entireties are hereby incorporated by reference in this application.

A number of embodiments have been described. Nevertheless, it will be understood that various modifications may be made. Accordingly, other embodiments are within the scope of the following claims.

What is claimed is:

1. A method for identifying a nucleotide in a template nucleic acid, comprising
    (a) providing a plurality of primer-template nucleic acid hybrids, wherein the primers comprise an extendable 3' end;
    (b) after step (a) contacting the plurality with:
        (i) blocked nucleotides to produce a first subset of the primer-template nucleic acid hybrids that each comprise a blocked nucleotide at the 3' end, and
        (ii) a ternary complex inhibitor to produce a second subset of the primer-template nucleic acid hybrids that each comprise a ternary complex inhibitor;
    (c) after steps (a) and (b) forming ternary complexes that each comprise a polymerase, a primer-template nucleic acid hybrid of the first subset, and a cognate nucleotide, wherein the cognate nucleotide is a cognate of a next base of the template nucleic acid; and
    (d) after steps (a), (b) and (c) detecting the ternary complexes, thereby identifying a nucleotide in the template nucleic acid.

2. The method of claim 1, wherein the blocked nucleotides comprise reversibly terminated nucleotides and wherein the primer-template nucleic acid hybrids in the first subset of the primer-template nucleic acid hybrids each comprise a reversibly terminated nucleotide at the 3' end.

3. The method of claim 2, further comprising
    (e) deblocking the reversibly terminated nucleotide at the 3' end of the primer-template nucleic acid hybrids in the first subset.

4. The method of claim 3, further comprising
    (f) repeating steps (b) through (e) to sequence template nucleic acids in the first subset.

5. The method of claim 4, further comprising removing the polymerase and cognate nucleotide from the primer-template nucleic acid hybrids of the first subset prior to step (f).

6. The method of claim 4, wherein steps (b) through (f) are repeated so long as the number of the primer-template nucleic acid hybrids in the first subset is more than 50% of the plurality of primer-template nucleic acid hybrids.

7. The method of claim 4, wherein steps (b) through (f) are repeated at least 100 times.

8. The method of claim 1, wherein the second subset of primer-template nucleic acid hybrids comprises less than 1% of the plurality of primer-template nucleic acid hybrids.

9. The method of claim 1, wherein the plurality of primer-template nucleic acid hybrids is attached to a solid support.

10. The method of claim 9, wherein the plurality of primer-template nucleic acid hybrids is attached to a feature of an array.

11. The method of claim 10, wherein the plurality of primer-template nucleic acid hybrids that is attached to the feature comprises at least 100 copies having a common sequence.

12. The method of claim 10, wherein the primer-template nucleic acid hybrids that are attached to the feature are detected as an ensemble.

13. The method of claim 9, wherein the plurality of primer-template nucleic acid hybrids comprises different templates that are attached to different features of an array.

14. The method of claim 1, wherein the ternary complex inhibitor comprises an oligonucleotide moiety.

15. The method of claim 14, wherein the oligonucleotide moiety is produced by ligating an oligonucleotide to the primer-template nucleic acid hybrids in step (b).

16. The method of claim 14, wherein the oligonucleotide moiety is produced by polymerase-catalyzed extension of the primer-template nucleic acid hybrids in step (b).

17. The method of claim 1, wherein unreacted blocked nucleotides are separated from the plurality of primer-template nucleic acid hybrids after step (b)(i).

18. The method of claim 17, wherein unreacted blocked nucleotides are separated from the plurality of primer-template nucleic acid hybrids before step (b)(ii).

* * * * *